(12) United States Patent
Gibbs et al.

(10) Patent No.: US 9,751,897 B1
(45) Date of Patent: Sep. 5, 2017

(54) DERIVATIVES OF BODIPY

(71) Applicants: Summer Gibbs, Portland, OR (US); Amy Bittel, Portland, OR (US); Xiaolin Nan, Portland, OR (US)

(72) Inventors: Summer Gibbs, Portland, OR (US); Amy Bittel, Portland, OR (US); Xiaolin Nan, Portland, OR (US)

(73) Assignee: Oregon Health & Science University, Portland, OR (US)

( * ) Notice: Subject to any disclaimer, the term of this patent is extended or adjusted under 35 U.S.C. 154(b) by 0 days.

(21) Appl. No.: 15/430,384

(22) Filed: Feb. 10, 2017

Related U.S. Application Data

(60) Provisional application No. 62/294,624, filed on Feb. 12, 2016.

(51) Int. Cl.
*C07F 5/02* (2006.01)

(52) U.S. Cl.
CPC ............ *C07F 5/022* (2013.01); *C07F 5/025* (2013.01)

(58) Field of Classification Search
CPC .............................. C07F 5/0006; C07F 5/022
See application file for complete search history.

(56) References Cited

U.S. PATENT DOCUMENTS

| | | | | |
|---|---|---|---|---|
| 5,512,486 A * | 4/1996 | Giese | ............ | C07F 5/022 436/103 |
| 5,614,386 A * | 3/1997 | Metzker | ............ | C07H 21/00 435/5 |
| 6,972,326 B2 * | 12/2005 | Haugland | ............ | C07K 1/1077 435/7.5 |

FOREIGN PATENT DOCUMENTS

| | | | | |
|---|---|---|---|---|
| SG | WO2012071012 | | 5/2012 | |
| SG | WO2014088512 | | 6/2014 | |
| WO | WO9309185 | | 5/1993 | |
| WO | WO 9309185 A1 * | 5/1993 | ............ | C07F 5/022 |
| WO | WO 2014088512 A1 * | 6/2014 | ......... | G01N 21/6428 |

OTHER PUBLICATIONS

D. Zhai et al., 14 ACS Combinatorial Science, 81-84 (2012).*
Chemical Abstract Compound, STN Express, RN 150173-89-0 (Sep. 22, 1993), RN 749180-51-6 (Sep. 22, 2004), 1 page.
Meltola, et al., "Hydrophilic Labeling Reagents of Dipyrylmethene-BF2 Dyes for Two-Photon Excited Fluorometry: Syntheses and Photophysical Characterization", Journal of Fluorescence, vol. 14, No. 5, 2004, pp. 635-647.
PCT Search Report and Written Opinion dated May 19, 2017 for International Application No. PCT/US2017/017542.

* cited by examiner

*Primary Examiner* — Alexander R Pagano
(74) *Attorney, Agent, or Firm* — Lee & Hayes, PLLC

(57) ABSTRACT

Derivatives of BODIPY with improved properties (such as longer Stokes shift relative to existing fluorophores) are disclosed.

25 Claims, 11 Drawing Sheets

DERIVATIVES OF BODIPY

CROSS-REFERENCE TO RELATED APPLICATION

This application claims the benefit of U.S. Provisional Patent Application 62/294,624, filed Feb. 12, 2016, and entitled DERIVATIVES OF BODIPY, the entire disclosure of which is incorporated by reference herein.

BACKGROUND OF THE DISCLOSURE

Single-molecule localization microscopy (SMLM) utilizes photoswitchable fluorophores to detect biological entities with 10-20 nm resolution. Multispectral superresolution microscopy (MSSRM) extends SMLM functionality by improving its spectral resolution up to 5 fold facilitating imaging of multicomponent cellular structures or signaling pathways. Current commercial fluorophores are not ideal for MSSRM as they are not designed to photoswitch and do not adequately cover the visible and far-red spectral regions required for MSSRM imaging. To obtain optimal MSSRM spatial and spectral resolution, fluorophores with narrow emission spectra and controllable photoswitching properties are necessary.

SUMMARY OF THE DISCLOSURE

Disclosed are compounds with the structure:

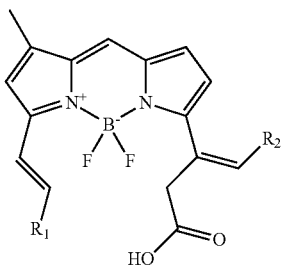

where $R_1$ is an aryl, a substituted aryl, an aromatic heterocycle, or a substituted aromatic heterocycle and $R_2$ is H, an aryl, a substituted aryl, an aromatic heterocycle, or a substituted aromatic heterocycle. In examples, $R_2$ is H, a substituted aryl, or a substituted aromatic heterocycle.

In further examples, the compounds have the structure:

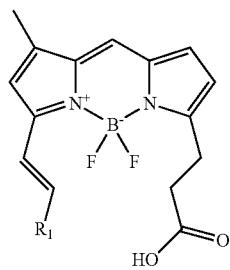

where $R_1$ is an aryl, a substituted aryl, an aromatic heterocycle, or substituted aromatic heterocycle. In examples, $R_1$ is a substituted aryl or a substituted aromatic heterocycle. In examples, $R_1$ is a substituted or unsubstituted quinolinyl, indolyl, benzyl, naphthyl, pyrimidinyl, thiophenyl, pyrazolyl, thiazolyl, pyridinyl, or furanyl. In further examples $R_1$ is a substituted quinolinyl, indolyl, benzyl, naphthyl, pyrimidinyl, thiophenyl, pyrazolyl, thiazolyl, pyridinyl, or furanyl.

In still further examples, the compounds have the structure:

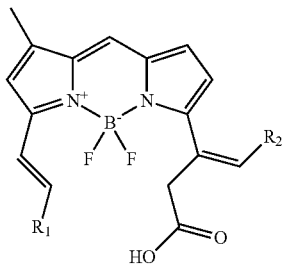

where $R_1$ and $R_2$ are independently substituted or unsubstituted quinolinyl, isoquinolinyl, indolyl, benzyl, naphthyl, pyrimidinyl, thiophenyl, pyrazolyl, thiazolyl, pyridinyl, or furanyl. In other examples, $R_1$ and $R_2$ are both substituted or unsubstituted quinolinyl, isoquinolinyl, indolyl, benzyl, naphthyl, pyrimidinyl, thiophenyl, pyrazolyl, thiazolyl, pyridinyl, or furanyl. In still other examples, $R_1$ is the same structure as $R_2$. Specific examples of $R_1$ and $R_2$ groups are shown in Table 1 herein.

It is an object of the invention to provide fluorophores with narrow emission spectra and controllable photoswitching properties.

BRIEF DESCRIPTION OF THE SEVERAL VIEWS OF THE DRAWINGS

Some of the drawings are better understood when presented in color. Applicants consider the color drawings to be part of the original disclosure and reserve the right to present color versions of the drawings in later proceedings.

FIG. 7A shows the molecular orbitals of BAA-37a.
FIG. 7D shows the molecular orbitals of BAA-5a FIG. 7E shows the molecular orbitals of BAA-2a
FIG. 7F shows the molecular orbitals of BAA-39a.

DETAILED DESCRIPTION

Figure 1A:
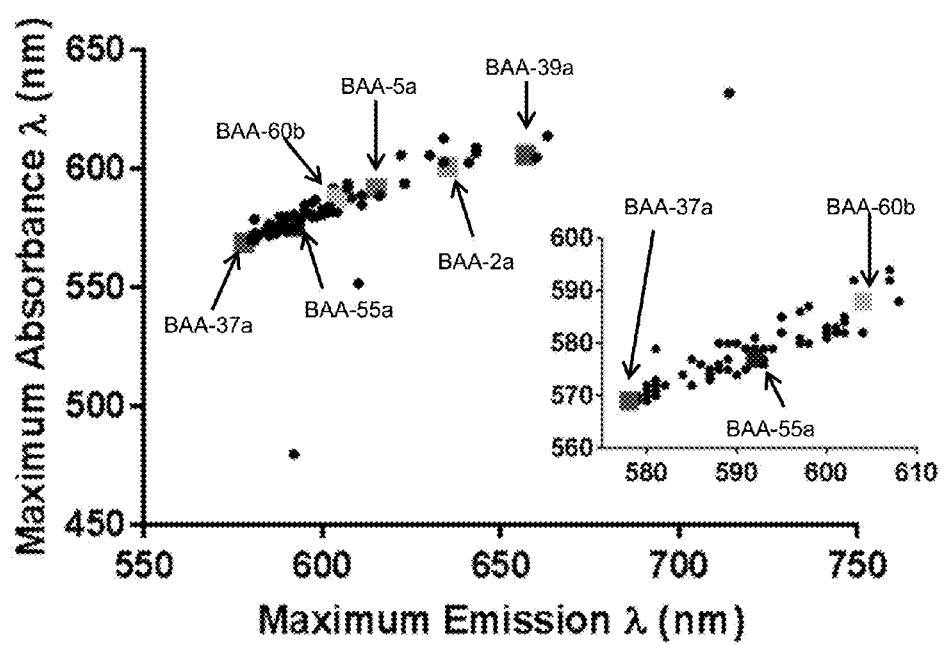
FIG. 1A is a plot showing the maximum absorbance vs maximum emission wavelength for all of the compounds in the BAA library. Particular compounds are indicated by arrows. The inset is a higher resolution view with three indicated compounds.
Figure 1B:
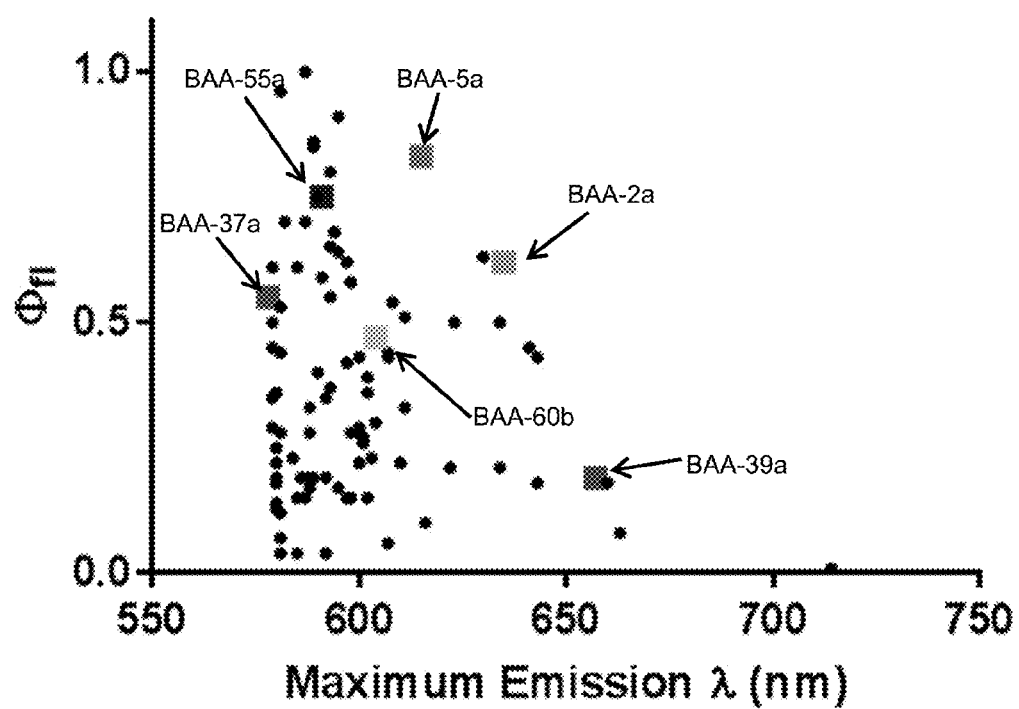
FIG. 1B is a plot showing the quantum yield vs maximum emission wavelength for all of the compounds in the BAA library. Particular compounds are indicated by arrows.
Figure 1C:
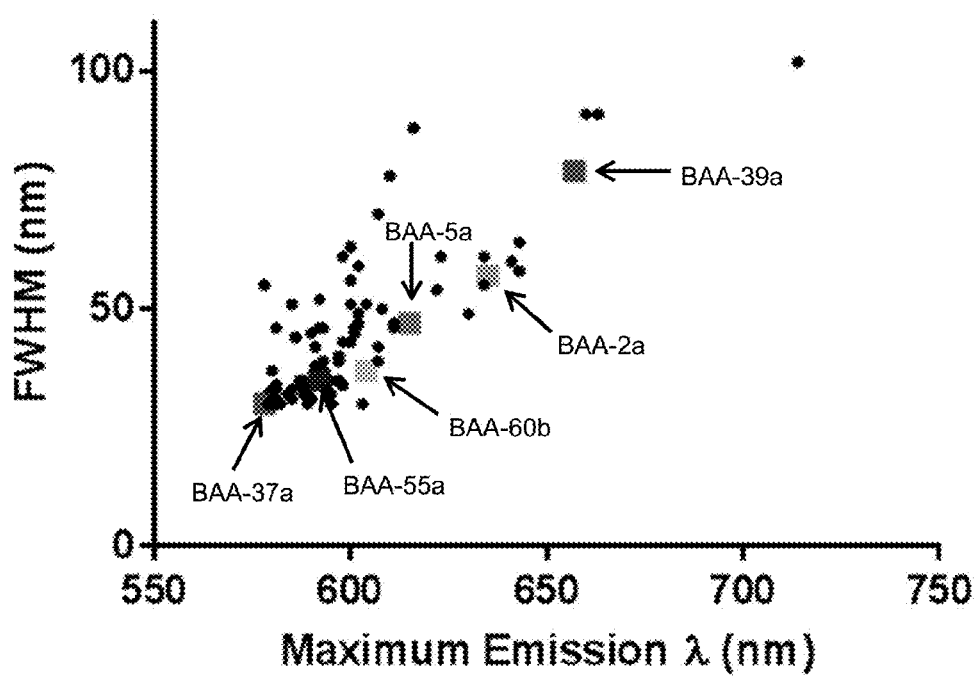
FIG. 1C is a plot showing the full width at half max vs maximum emission wavelength for all of the compounds in the BAA library. Particular compounds are indicated by arrows.
Figure 2A:
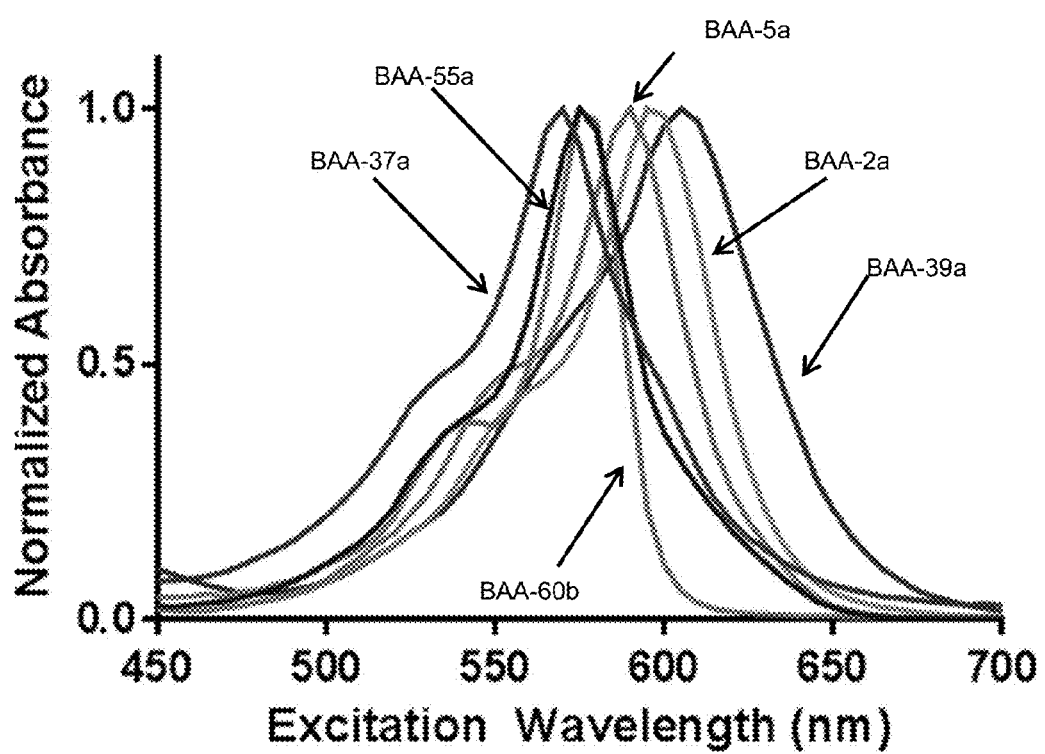
FIG. 2A is a plot of the absorbance spectra of the indicated compounds.
Figure 2B:
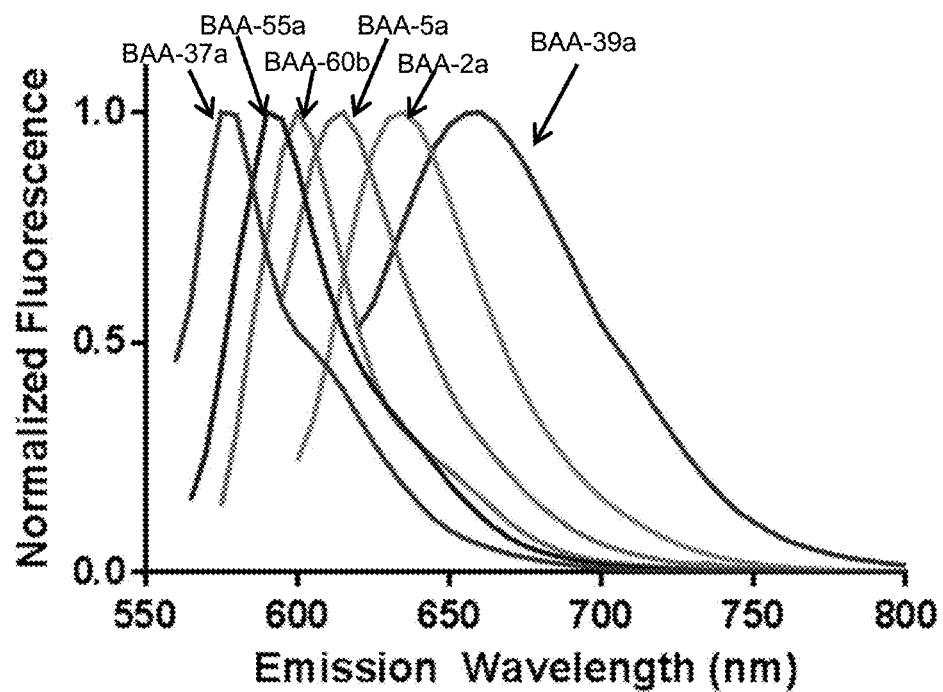
FIG. 2B is a plot of the emission spectra of the indicated compounds.
Figure 3:
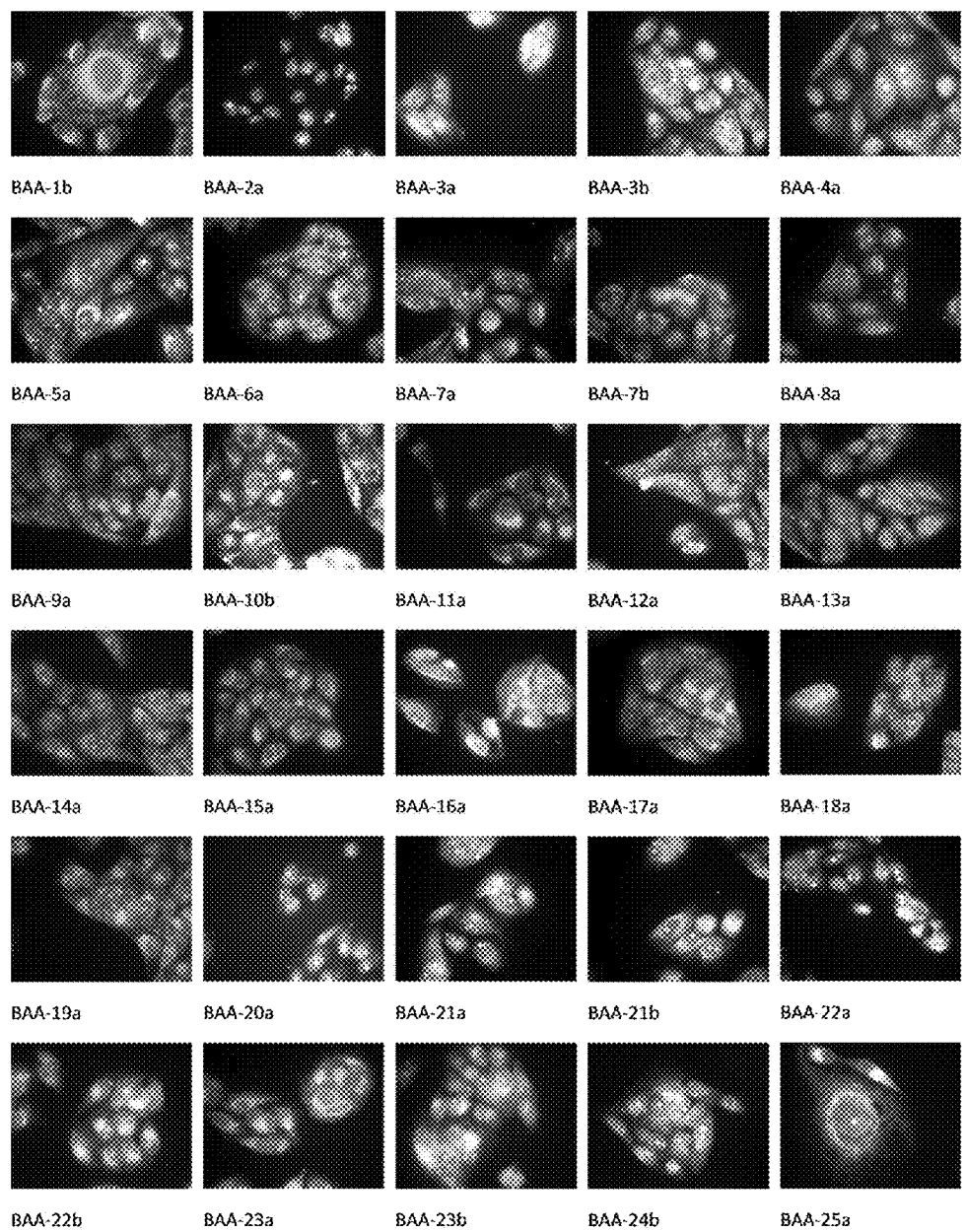
FIG. 3 is a set of images showing the organelle specificity of the indicated compounds in fixed U2OS cells.
Figure 4:
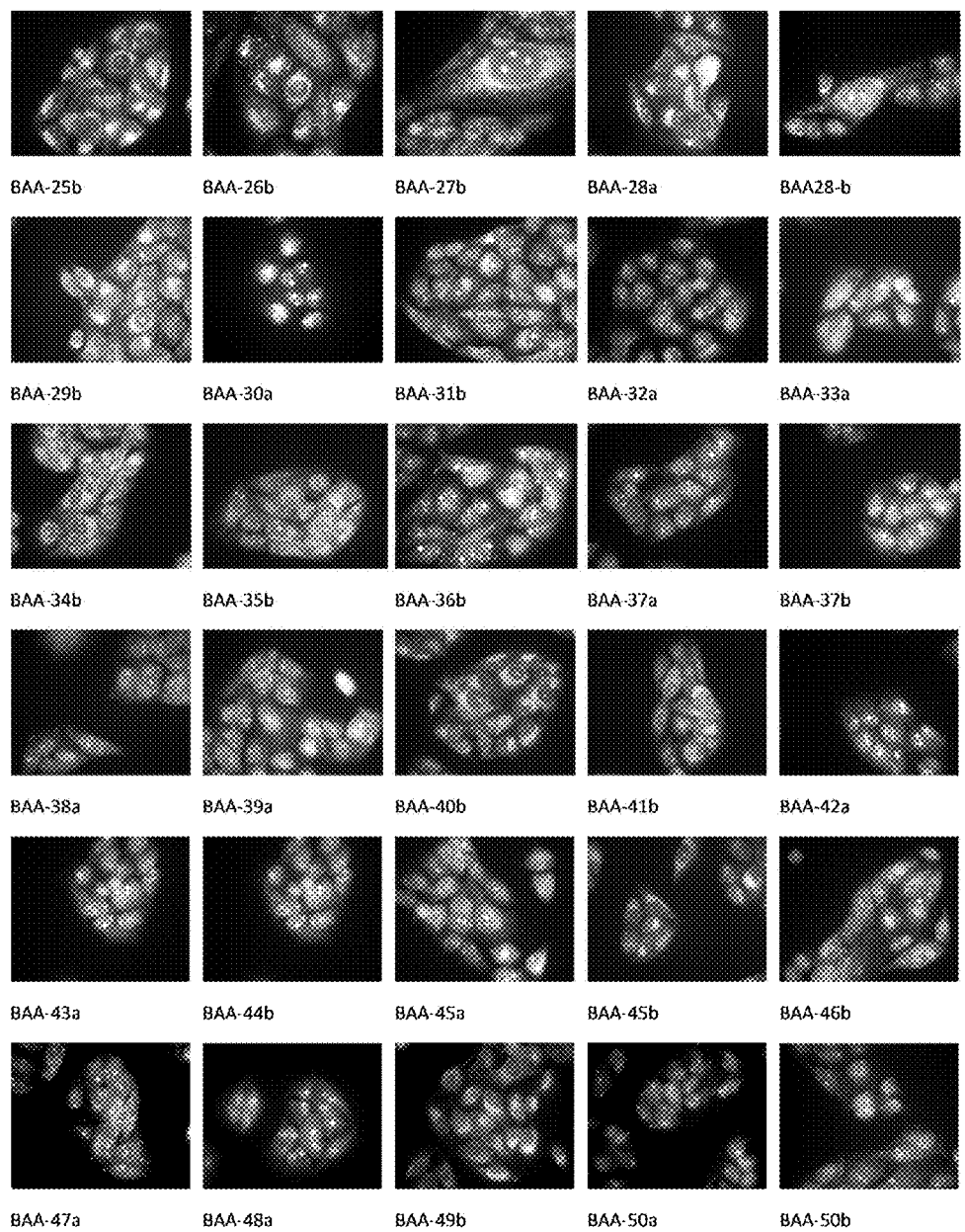
FIG. 4 is a set of images showing the organelle specificity of the indicated compounds in fixed U2OS cells.
Figure 5:
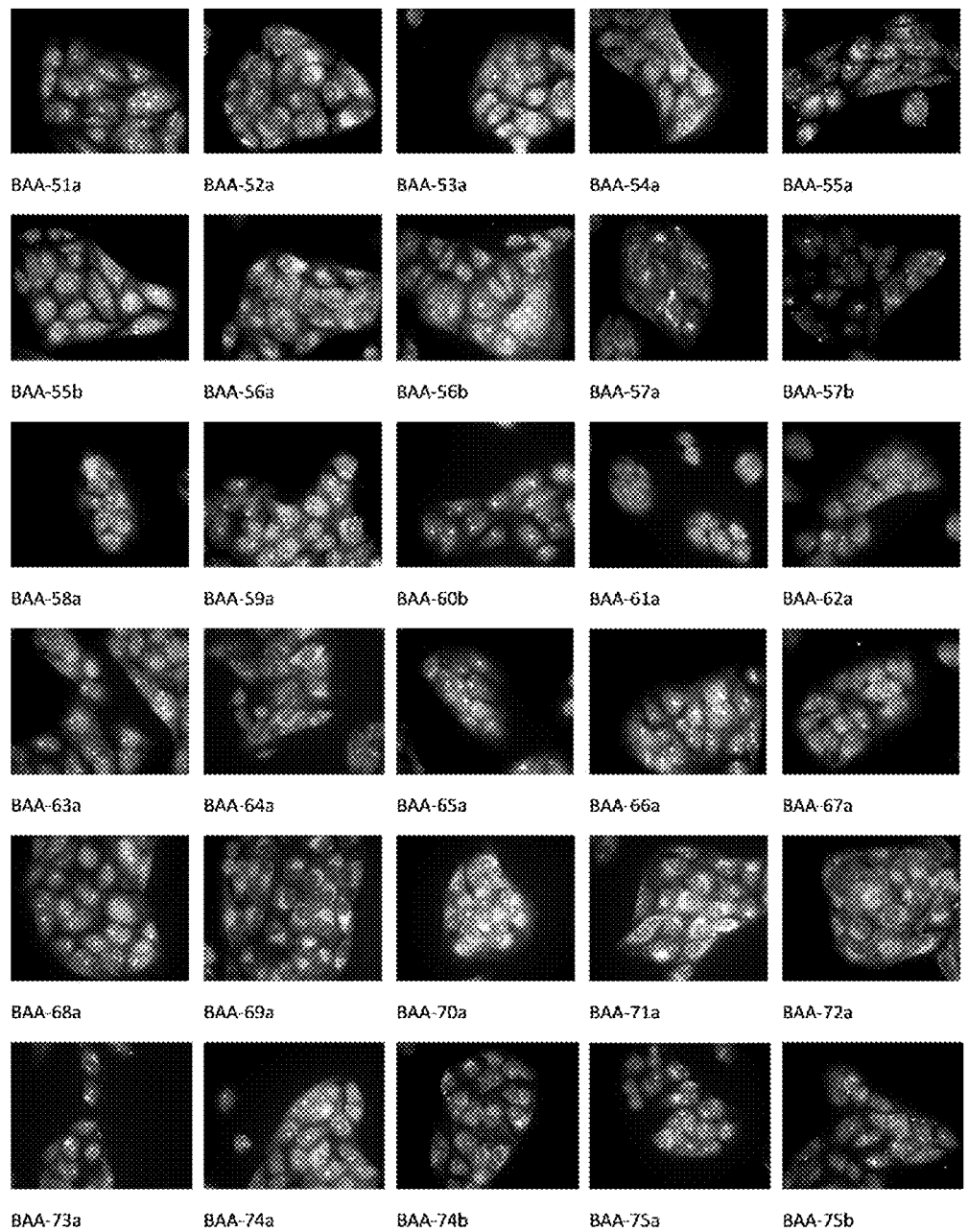
FIG. 5 is a set of images showing the organelle specificity of the indicated compounds in fixed U2OS cells.
Figure 6:
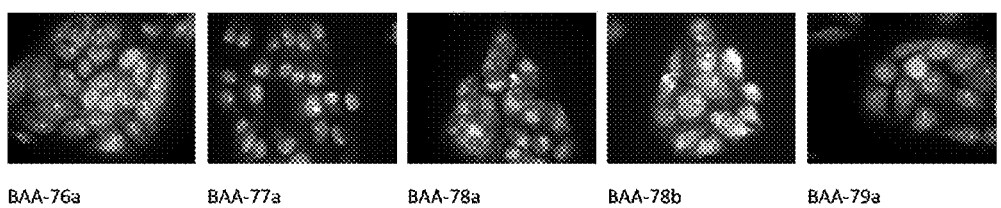
FIG. 6 is a set of images showing the organelle specificity of the indicated compounds in fixed U2OS cells.
Figure 7A:
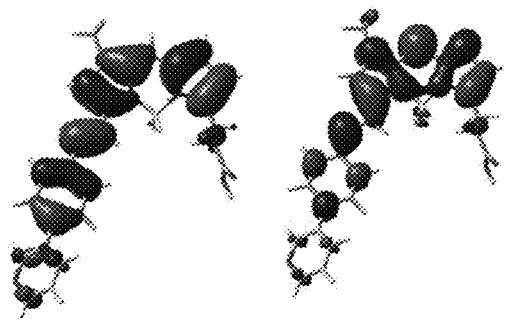
Figure 7B:
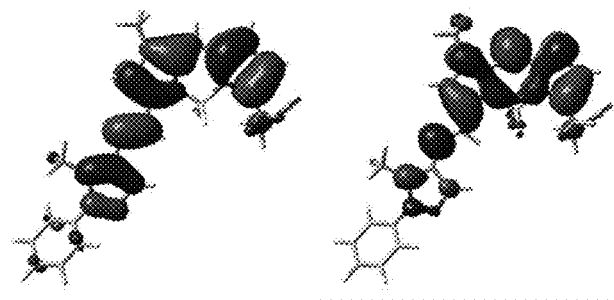
FIG. 7B shows the molecular orbitals of BAA-55a
FIG. 7C shows the molecular orbitals of BAA-60b
Figure 7C:
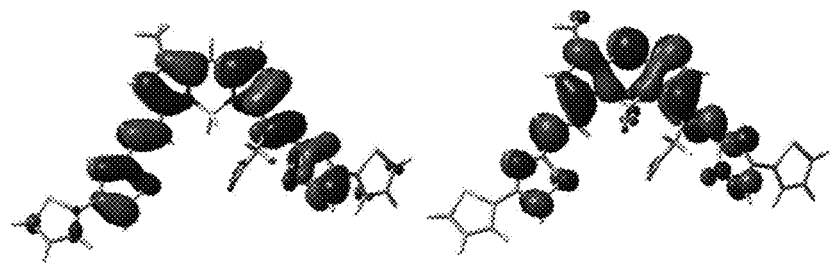
Figure 7D:
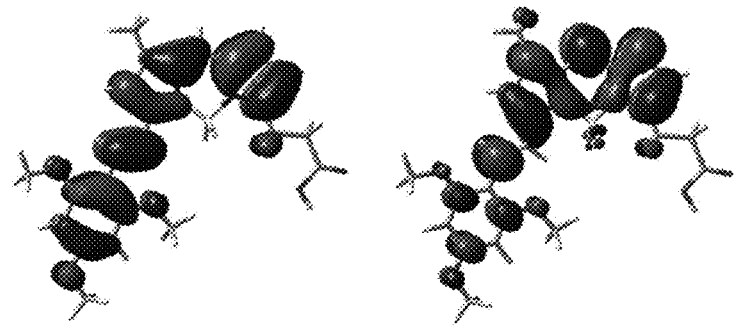
Figure 7E:
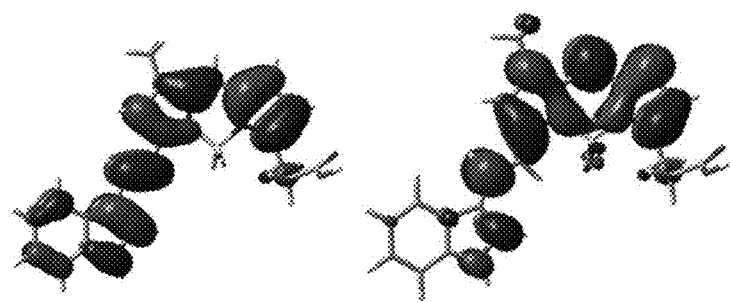
Figure 7F:
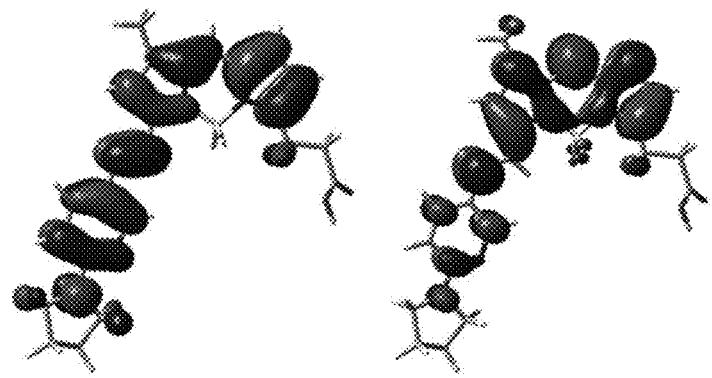

Herein, a library of BODIPY-based fluorophores was synthesized and characterized to create optimal photoswitchable fluorophores for MSSRM. BODIPY was chosen as the core structure as it is photostable, has high quantum yield, and controllable photoswitching. The BODIPY core was modified through the addition of various aromatic moieties, resulting in a spectrally diverse library. Photoswitching properties were characterized using a novel polyvinyl alcohol (PVA) based film methodology to isolate single molecules. The PVA film methodology enabled photoswitching assessment without the need for protein conjugation, greatly improving screening efficiency of the BODIPY library. Additionally, image buffer conditions were optimized for the BODIPY-based fluorophores through systematic testing of oxygen scavenger systems, redox components, and additives. Through screening the photoswitching properties of BODIPY-based compounds in PVA films with optimized imaging buffer we identified novel fluorophores well suited for SMLM and MSSRM. Such compounds have longer Stokes shifts than commercial fluorophores.

The disclosed compounds have the structure:

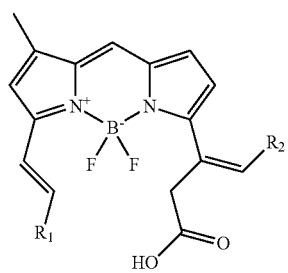

where $R_1$ is an aryl, a substituted aryl, an aromatic heterocycle, or a substituted aromatic heterocycle and $R_2$ is H, an aryl, a substituted aryl, an aromatic heterocycle, or a substituted aromatic heterocycle. In examples, $R_2$ is H, a substituted aryl, or a substituted aromatic heterocycle. In further examples, the compounds have the structure:

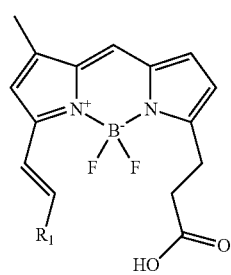

where $R_1$ is an aryl, a substituted aryl, an aromatic heterocycle, or a substituted aromatic heterocycle. In examples, $R_1$ is a substituted aryl or a substituted aromatic heterocycle. In examples, $R_1$ is a substituted or unsubstituted quinolinyl, indolyl, benzyl, naphthyl, pyrimidinyl, thiophenyl, pyrazolyl, thiazolyl, pyridinyl, or furanyl. In further examples, $R_1$ is a substituted quinolinyl, indolyl, benzyl, naphthyl, pyrimidinyl, thiophenyl, pyrazolyl, thiazolyl, pyridinyl, or furanyl.

The compounds are synthesized by attaching an aromatic aldehyde of general structure:

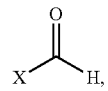

where X is a substituted aryl, aromatic heterocycle or substituted aromatic heterocycle to BODIPY via the following scheme.

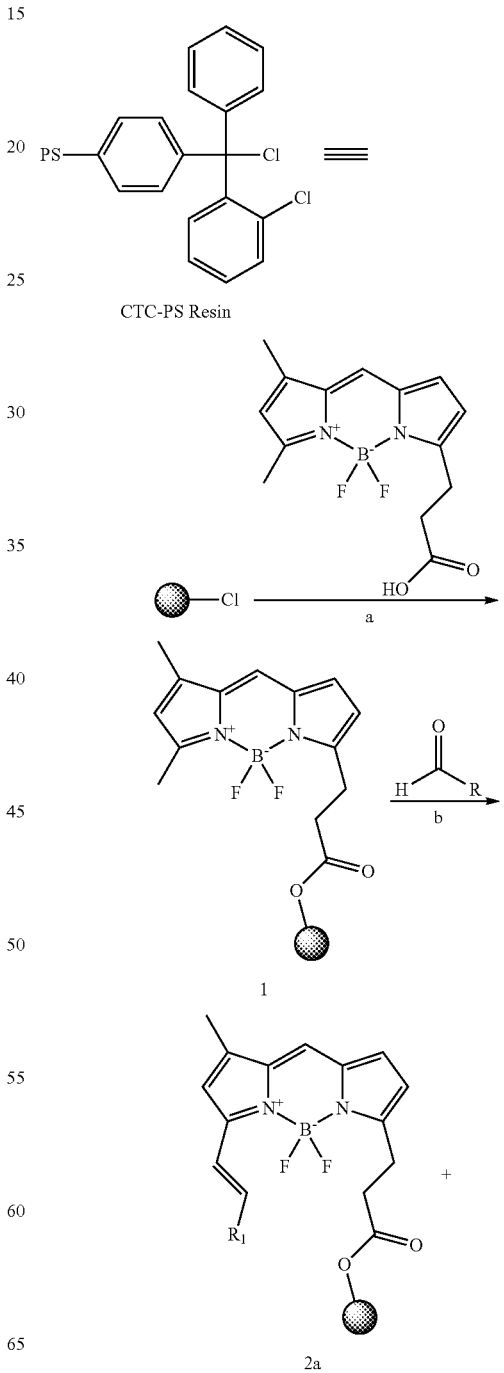

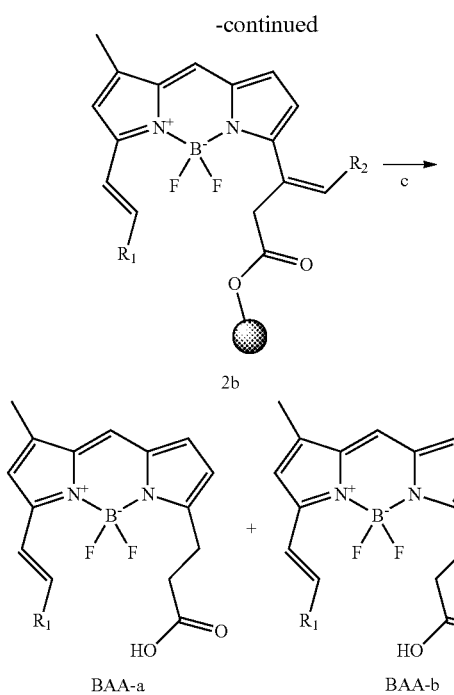

where the aromatic aldehyde is indicated in the scheme by the following structure:

Reaction (a) is performed in the presence of DCM and DIEA, at room temperature for 20 h. In reaction (b) R-CHO are added in the presence of DMSO-ACN (1:1), pyrrolidine, acetic acid, at 85° C. for 15 min; (c) TFA-DCM (0.5:99.5), rt, 2×10 min.

More specifically, BODIPY FL was loaded onto CTC-PS resin in the following increments: 500 mg of BODIPY FL in 17.2 ml of DCM was added to 5 g of CTC-PS resin in 14.9 ml of DIEA, protected from light, and placed on the shaker overnight. This was washed 3 times in dichloromethane (DCM), 3 times in dimethylformamide (DMF), 3 times in methanol, 3 additional times in DMF, 3×DCM and dried with ethyl ether, resulting in 90% BODIPY FL retained on the resin.

The BODIPY FL loaded CTC-PS resin (100 mg in 3 ml of a 1:1 mixture of dimethylsulfoxide (DMSO) and acetonitrile (ACN)) and 15 equivalents of aldehyde solution (0.45 mmol in 1 ml of a 1:1 mixture of DMSO and ACN) were mixed with 65 equivalents of acetic acid (105 µl, 2 mmol) and 65 equivalents of pyrrolidine (150 µl, 2 mmol) at 85° C. for 15 min. The resin was washed 3 times in DCM and 3 times in DMF—and this cycle (3×in DCM, 3× in DMF) was repeated three times. The resin was then washed 3× in ethyl ether before cleaving the formed BAA compound with 0.5% TFA in DCM. The BAA compounds were purified via HPLC and dried using a Labconco freeze dryer.

Specific structures and purity data are as follows:

| Product | $R_1$ | $R_2$ | m/z calc | m/z exp | RT (min) | Purity (%) |
|---|---|---|---|---|---|---|
| BAA-1b | 3-chloro-7-methoxyisoquinolin-4-yl | =$R_1$ | 698.15 | 699.15 | 7.83 | 92 |
| BAA-2a | 5-methoxy-1H-indol-3-yl | H | 419.16 | 400.16$^a$ | 7.66 | >99 |
| BAA-3a | 3-iodo-4,5-dimethoxyphenyl | H | 566.07 | 567.95 | 8.07 | 98 |

-continued

| Product | R₁ | R₂ | m/z calc | m/z exp | RT (min) | Purity (%) |
|---|---|---|---|---|---|---|
| BAA-3b | 3,4-dimethoxy-5-iodophenyl | =R₁ | 840.02 | 863.25[b] | 8.21 | 97 |
| BAA-4a | 2-(4-methylpiperazin-1-yl)phenyl | H | 478.24 | 479.24 | 6.02 | >99 |
| BAA-5a | 2,4,6-trimethoxyphenyl | H | 470.18 | 471.19 | 8.26 | >99 |
| BAA-6a | 5-methoxy-3H-indol-3-yl | H | 449.17 | 472.18[b] | 7.69 | 82 |
| BAA-7a | 2,4-dimethoxy-3-methylphenyl | H | 454.19 | 477.27[b] | 8.64 | 83 |
| BAA-7b | 2,4-dimethoxy-3-methylphenyl | =R₁ | 616.26 | 617.26 | 7.32 | 88 |
| BAA-8a | 4-methoxynaphthalen-1-yl | H | 460.18 | 461.19 | 8.31 | 80 |

-continued

| Product | R₁ | R₂ | m/z calc | m/z exp | RT (min) | Purity (%) |
|---|---|---|---|---|---|---|
| BAA-9a | 2-borono-4-methoxyphenyl | H | 454.17 | 455.13 | 8.15 | 92 |
| BAA-10b | 4-(diethylamino)phenyl | =R₁ | 610.33 | 611.35 | 9.45 | >99 |
| BAA-11a | 4-ethoxy-3,5-dimethylphenyl | H | 514.22 | 515.22 | 8.98 | 91 |
| BAA-12a | 2-(propylthio)pyrimidin-5-yl | H | 456.16 | 474.19[c] | 7.69 | 88 |
| BAA-13a | 3-fluoro-4-methoxyphenyl | H | 428.15 | 429.15 | 7.28 | 90 |
| BAA-14a | 5-isobutylthiophen-2-yl | H | 442.17 | 465.16[b] | 9.15 | 83 |

-continued

| Product | R₁ | R₂ | m/z calc | m/z exp | RT (min) | Purity (%) |
|---|---|---|---|---|---|---|
| BAA-15a | 4-methoxy-3-allylphenyl | H | 450.19 | 451.19 | 8.83 | 96 |
| BAA-16a | 2,4,5-trimethylphenyl | H | 422.2 | 445.19[b] | 9.08 | 98 |
| BAA-17a | biphenyl-4-yl | H | 456.18 | 479.17[b] | 9.09 | 85 |
| BAA-18a | 4-(benzyloxy)phenyl | H | 486.19 | 509.18[b] | 8.94 | 92 |
| BAA-19a | 4-(thiophen-2-yl)phenyl | H | 462.14 | 485.13 | 8.94 | 96 |
| BAA-20a | 2-(ethylthio)pyrimidin-5-yl | H | 442.14 | 443.15 | 8.07 | 98 |

-continued
| Product | R₁ | R₂ | m/z calc | m/z exp | RT (min) | Purity (%) |
|---|---|---|---|---|---|---|
| BAA-21a | 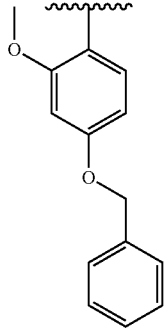 | H | 516.2 | 497.21[a] | 9.13 | 95 |
| BAA-21b | 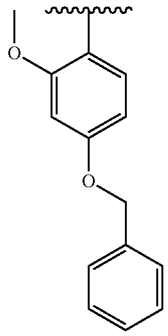 | =R₁ | 740.29 | 741.29 | 7.82 | 92 |
| BAA-22a | 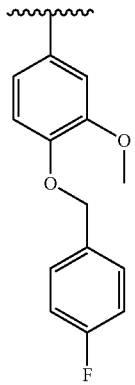 | H | 534.19 | 515.20[a] | 8.65 | 94 |
| BAA-22b | 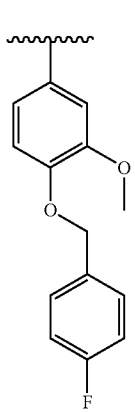 | =R₁ | 776.27 | 777.28 | 7.51 | 90 |

| Product | R₁ | R₂ | m/z calc | m/z exp | RT (min) | Purity (%) |
|---|---|---|---|---|---|---|
| BAA-23a | 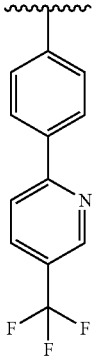 | H | 525.16 | 526.18 | 9.05 | >99 |
| BAA-23b | 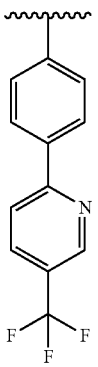 | =R₁ | 758.21 | 739.13 | 7.93 | 89 |
| BAA-24b | 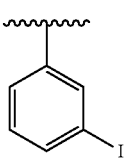 | =R₁ | 719.98 | 700.98[a] | 7.46 | 94 |
| BAA-25a | 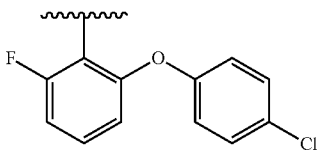 [SMILES: *c1c(F)cccc1Oc1ccc(Cl)cc1] | H | 524.73 | 547.12[b] | 9.30 | 93 |
| BAA-25b | 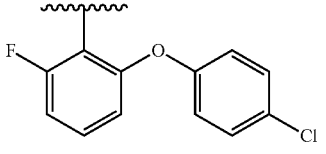 [SMILES: *c1c(F)cccc1Oc1ccc(Cl)cc1] | =R₁ | 756.14 | 757.15 | 7.88 | 95 |
| BAA-26b | 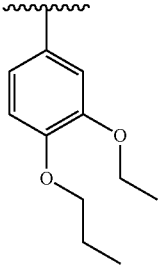 [SMILES: *c1ccc(OCCC)c(OCC)c1] | =R₁ | 672.32 | 673.33 | 7.56 | 98 |

-continued
| Product | R₁ | R₂ | m/z calc | m/z exp | RT (min) | Purity (%) |
|---|---|---|---|---|---|---|
| BAA-27b | 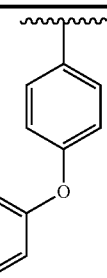 | =R₁ | 720.16 | 683.22 | 7.19 | 97 |
| BAA-28a | 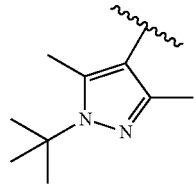 [SMILES: *c1c(C)nn(C(C)(C)C)c1C] | H | 454.24 | 435.28 | 6.69 | 88 |
| BAA-28b | 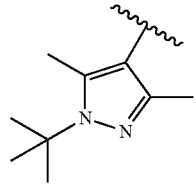 | =R₁ | 616.35 | 617.37 | 6.99 | 97 |
| BAA-29b | 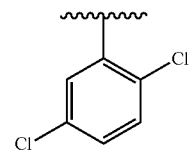 [SMILES: *c1cc(Cl)ccc1Cl] | =R₁ | 604.03 | 605.03 | 8.14 | 86 |
| BAA-30a | 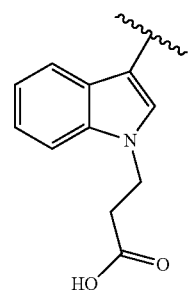 [SMILES: *c1cn(CCC(=O)O)c2ccccc12] | H | 491.18 | 492.19 | 7.41 | 96 |
| BAA-31b | 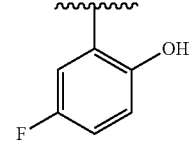 | =R₁ | 536.28 | 497.15[d] | 6.34 | 94 |
| BAA-32a | 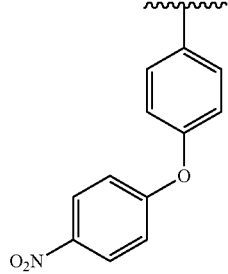 [SMILES: *c1ccc(Oc2ccc([N+](=O)[O-])cc2)cc1] | H | 517.16 | 478.15[d] | 8.77 | >99 |

-continued
| Product | R₁ | R₂ | m/z calc | m/z exp | RT (min) | Purity (%) |
|---|---|---|---|---|---|---|
| BAA-33a | 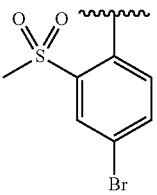 [SMILES: *c1ccc(Br)cc1S(C)(=O)=O] | H | 536.04 | 559.02[b] | 7.94 | 98 |
| BAA-34b | 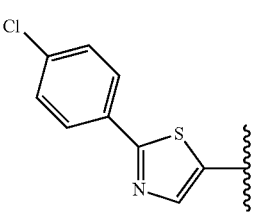 [SMILES: *c1cnc(-c2ccc(Cl)cc2)s1] | =R₁ | 702.07 | 683.06[a] | 7.69 | 94 |
| BAA-35b | 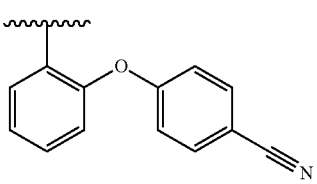 [SMILES: *c1ccccc1Oc1ccc(C#N)cc1] | =R₁ | 702.22 | 703.15 | 8.49 | 86 |
| BAA-36b | 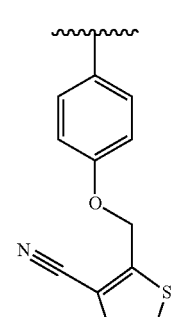 | =R₁ | 742.17 | 743.18 | 8.16 | 94 |
| BAA-37a | 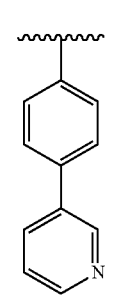 | H | 457.18 | 438.18[a] | 5.75 | 88 |
| BAA-37b | 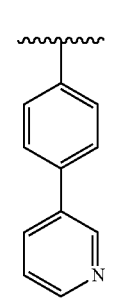 | =R₁ | 622.24 | 623.24 | 5.78 | >99 |

-continued
| Product | R₁ | R₂ | m/z calc | m/z exp | RT (min) | Purity (%) |
|---|---|---|---|---|---|---|
| BAA-38a | 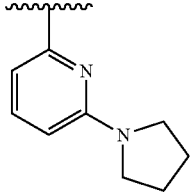 [SMILES: *c1cccc(N2CCCC2)n1] | H | 450.2 | 451.21 | 6.28 | 99 |
| BAA-39a | 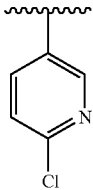 | H | 415.11 | 451.21[g] | 5.99 | 94 |
| BAA-40b | 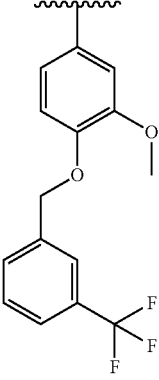 | =R₁ | 876.26 | 877.27 | 7.96 | 89 |
| BAA-41b | 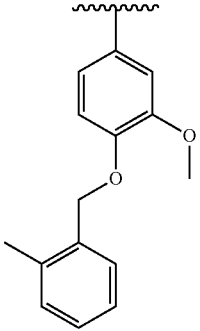 | =R₁ | 768.32 | 769.33 | 7.61 | 94 |
| BAA-42a | 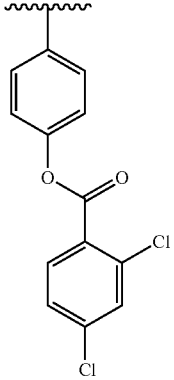 [SMILES: *c1ccc(OC(=O)c2ccc(Cl)cc2Cl)cc1] | H | 568.09 | 501.17[a] | 6.17 | 82 |

-continued
| Product | R₁ | R₂ | m/z calc | m/z exp | RT (min) | Purity (%) |
|---|---|---|---|---|---|---|
| BAA-43a | 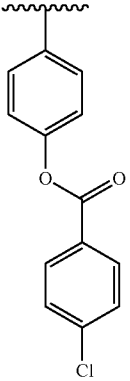 | H | 534.13 | 501.17[f] | 6.13 | 94 |
| BAA-44b | 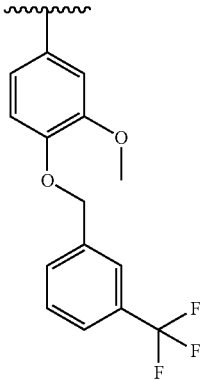 [SMILES: *c1ccc(OCc2cccc(C(F)(F)F)c2)c(OC)c1] | =R₁ | 876.26 | 877.27 | 8.15 | 92 |
| BAA-45a | 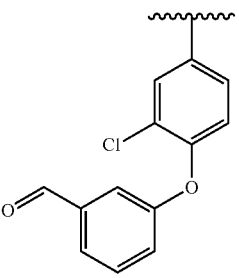 [SMILES: *c1ccc(Oc2cccc(C=O)c2)c(Cl)c1] | H | 538.75 | 562.14[b] | 9.29 | >99 |
| BAA-45b | 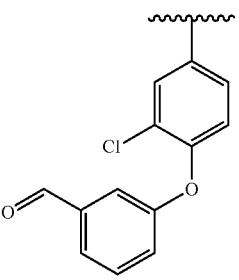 [SMILES: *c1ccc(Oc2cccc(C=O)c2)c(Cl)c1] | =R₁ | 784.17 | 785.17 | 8.24 | 96 |

-continued

| Product | R₁ | R₂ | m/z calc | m/z exp | RT (min) | Purity (%) |
|---|---|---|---|---|---|---|
| BAA-46b | 4-(3-methoxyphenoxy)phenyl | =R₁ | 740.29 | 741.28 | 7.69 | 94 |
| BAA-47a | 2,4-diethoxyphenyl | H | 468.2 | 491.20[b] | 8.62 | 94 |
| BAA-48a | 5-benzyloxy-1H-indol-3-yl | H | 525.2 | 548.19[b] | 8.24 | >99 |
| BAA-49b | 2-methoxy-5-[(ethoxycarbonylmethoxy)methyl]phenyl | =R₁ | 638.21 | 619.21[a] | 6.58 | >99 |
| BAA-50a | 3-(imidazol-1-yl)-6-methylphenyl | H | 460.19 | 483.18[b] | 8.07 | >99 |
| BAA-50b | 3-(imidazol-1-yl)-6-methylphenyl | =R₁ | 628.26 | 629.25 | 6.94 | >99 |

-continued

| Product | R₁ | R₂ | m/z calc | m/z exp | RT (min) | Purity (%) |
|---|---|---|---|---|---|---|
| BAA-51a | 6-ethoxyquinolin-2(1H)-on-4-yl | H | 491.18 | 514.16[b] | 7.59 | 89 |
| BAA-52a | 3-chloro-4-methoxy-4-(prop-2-yn-1-yloxy)phenyl | H | 498.13 | 499.12 | 7.86 | 83 |
| BAA-53a | 3,5-dimethoxyphenyl | H | 440.17 | 441.17 | 7.57 | >99 |
| BAA-54a | 4-chloro-3-fluorophenyl | H | 432.1 | 433.09 | 7.98 | 89 |
| BAA-55a | 5-methyl-1-phenyl-1H-pyrazol-4-yl | H | 460.19 | 461.18 | 7.30 | >99 |
| BAA-55b | 5-methyl-1-phenyl-1H-pyrazol-4-yl | =R₁ | 628.26 | 629.26 | 6.89 | 89 |
| BAA-56a | 6-(thiophen-2-yl)pyridin-3-yl | H | 463.13 | 464.13 | 5.87 | >99 |

-continued

| Product | R₁ | R₂ | m/z calc | m/z exp | RT (min) | Purity (%) |
|---|---|---|---|---|---|---|
| BAA-56b | (pyridine-thiophene) | =R₁ | 634.15 | 635.15 | 7.84 | 84 |
| BAA-57a | (4-(1-(2-methylphenyl)-5-methyl-pyrazolyl)) | H | 474.2 | 475.21 | 6.10 | 85 |
| BAA-57b | (4-(1-(2-methylphenyl)-5-methyl-pyrazolyl)) | =R₁ | 656.29 | 657.30 | 8.01 | >99 |
| BAA-58a | (methyl biphenyl-4-carboxylate) | H | 514.19 | 515.18 | 8.20 | >99 |
| BAA-59a | (6-(4-(methylsulfonyl)phenyl)pyridin-2-yl) | H | 535.15 | 553.16 | 7.37 | 96 |
| BAA-60b | (bithiophene) | =R₁ | 644.07 | 645.08 | 8.11 | 99 |

-continued

| Product | R₁ | R₂ | m/z calc | m/z exp | RT (min) | Purity (%) |
|---|---|---|---|---|---|---|
| BAA-61a | 4-methyl-2-(methoxymethyl)-6-boronic acid phenyl | H | 496.22 | 497.21 | 7.32 | 98 |
| BAA-62a | isoquinolin-5-yl | H | 431.16 | 449.16[c] | 6.81 | >99 |
| BAA-63a | 2-chloro-7-methylquinolin-3-yl | H | 479.14 | 502.15[b] | 7.05 | 93 |
| BAA-64a | 3-(4-chlorophenyl)-1H-pyrazol-4-yl | H | 480.13 | 481.11 | 7.50 | 91 |
| BAA-65a | 5-(2-fluorophenyl)furan-2-yl | H | 464.15 | 427.14[d] | 8.82 | 88 |
| BAA-66a | 6-(5-chlorothiophen-2-yl)pyridin-3-yl | H | 497.09 | 498.10 | 9.09 | 93 |
| BAA-67a | 6-(4-(ethylthio)phenyl)pyridin-3-yl | H | 517.18 | 518.18 | 9.02 | 92 |

-continued
| Product | R₁ | R₂ | m/z calc | m/z exp | RT (min) | Purity (%) |
|---|---|---|---|---|---|---|
| BAA-68a | 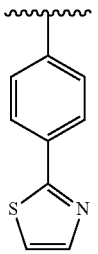 [SMILES: *c1ccc(-c2nccs2)cc1] | H | 463.13 | 464.14 | 8.27 | >99 |
| BAA-69a | 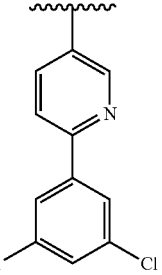 | H | 525.1 | 526.09 | 9.08 | >99 |
| BAA-70a | 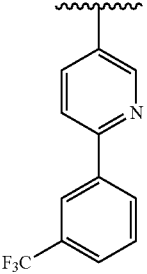 [SMILES: *c1ccc(-c2cccc(C(F)(F)F)c2)nc1] | H | 525.16 | 526.18 | 8.95 | 99 |
| BAA-71a | 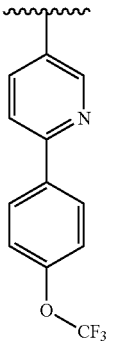 [SMILES: *c1ccc(-c2ccc(OC(F)(F)F)cc2)nc1] | H | 541.16 | 542.17 | 9.06 | >99 |
| BAA-72a | 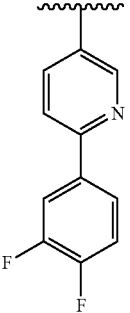 [SMILES: *c1ccc(-c2ccc(F)c(F)c2)nc1] | H | 493.16 | 511.17ᶜ | 8.13 | 98 |

-continued
| Product | R₁ | R₂ | m/z calc | m/z exp | RT (min) | Purity (%) |
|---|---|---|---|---|---|---|
| BAA-73a | 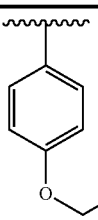 | H | 502.09 | 503.08 | 7.95 | >99 |
| BAA-74a | 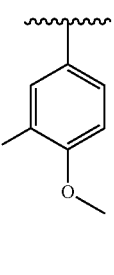 | H | 604.22 | 627.21[b] | 8.02 | 92 |
| BAA-74b | 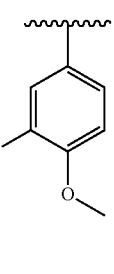 | =R₁ | 916.32 | 897.32[c] | 7.01 | 94 |
| BAA-75a | 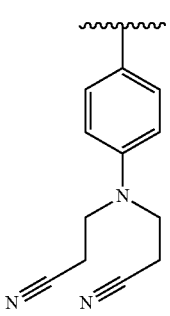 [SMILES: *c1ccc(N(CCC#N)CCC#N)cc1] | H | 501.21 | 482.22 | 10.99 | >99 |
| BAA-75b | 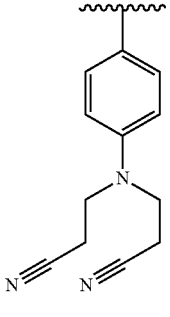 [SMILES: *c1ccc(N(CCC#N)CCC#N)cc1] | =R₁ | 710.31 | 711.32 | 6.38 | 94 |
| BAA-76a | 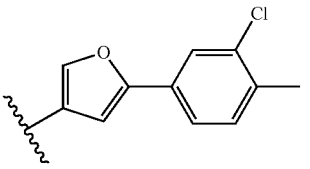 [SMILES: *c1coc(-c2ccc(C)c(Cl)c2)c1] | H | 510.13 | 491.13[a] | 90.31 | 98 |

-continued

| Product | R₁ | R₂ | m/z calc | m/z exp | RT (min) | Purity (%) |
|---|---|---|---|---|---|---|
| BAA-77a | 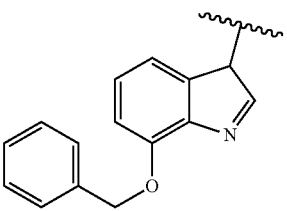 [SMILES: *C1C=Nc2c(OCc3ccccc3)cccc21] | H | 525.2 | 506.21[a] | 8.52 | 99 |
| BAA-78a | 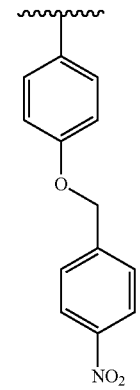 [SMILES: *c1ccc(OCc2ccc([N+](=O)[O-])cc2)cc1] | H | 531.18 | 512.18[a] | 8.72 | >99 |
| BAA-78b | 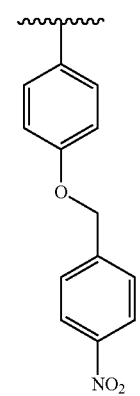 [SMILES: *c1ccc(OCc2ccc([N+](=O)[O-])cc2)cc1] | =R₁ | 770.24 | 771.24 | 7.73 | 98 |
| BAA-79a | 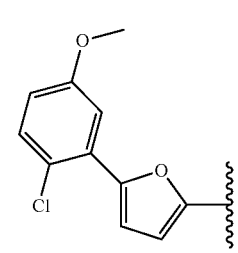 [SMILES: *c1ccc(-c2cc(OC)ccc2Cl)o1] | H | 494.14 | 457.13[d] | 9.421 | 91 |

LC/MS Conditions: A: H₂O—CH₂O₂: 99.9:0.1. B: ACN—CH₂O₂: 99.9:0.1; gradient 5% B to 30% B (1 min), gradient 30% B to 95% B (4.5 min), isocratic 95% B (4.5 min), flowrate: 0.4 ml/min. ESI (+) m/z signal found correspond to (M + H) except [a](M − F), [b](M + Na), [c](M + NH4), [d](M − 2F + H), [e](M − 2Cl + H), and [f](M − Cl); [g]Cl replaced by pyrrolidine during synthesis reaction. Purity was determined by integration of the LC/MS absorbance peaks at 254 nm.
=R₁ indicates that R₂ is the same structure as R₁.

Table 2 shows the spectroscopic properties of the BAA library:

| Product | λmax ABS (nm) | λmax EM (nm) | Stokes Shift (nm) | $\Phi_{fl}$ | FWHM |
|---|---|---|---|---|---|
| BAA-1b | 580 | 597 | 17 | 0.62 | 40 |
| BAA-2a | 601 | 635 | 34 | 0.62 | 57 |
| BAA-3a | 569 | 579 | 10 | 0.61 | 31 |
| BAA-3b | 574 | 587 | 13 | 0.70 | 34 |
| BAA-4a | 581 | 600 | 19 | 0.43 | 56 |
| BAA-5a | 592 | 615 | 23 | 0.83 | 47 |
| BAA-6a | 609 | 643 | 34 | 0.18 | 64 |
| BAA-7a | 582 | 600 | 18 | 0.29 | 63 |
| BAA-7b | 581 | 600 | 19 | 0.43 | 56 |
| BAA-8a | 594 | 623 | 29 | 0.50 | 61 |
| BAA-9a | 569 | 579 | 10 | 0.35 | 32 |
| BAA-10b | 632 | 714 | 82 | 0.01 | 102 |
| BAA-11a | 575 | 589 | 14 | 0.86 | 33 |
| BAA-12a | 589 | 616 | 27 | 0.10 | 88 |
| BAA-13a | 576 | 586 | 10 | 0.19 | 44 |
| BAA-14a | 594 | 607 | 13 | 0.44 | 70 |
| BAA-15a | 581 | 597 | 16 | 0.42 | 39 |
| BAA-16a | 552 | 610 | 58 | 0.22 | 78 |
| BAA-17a | 579 | 591 | 12 | 0.59 | 42 |
| BAA-18a | 577 | 593 | 16 | 0.65 | 37 |
| BAA-19a | 582 | 595 | 13 | 0.64 | 35 |
| BAA-20a | 577 | 585 | 8 | 0.15 | 31 |
| BAA-21a | 585 | 611 | 26 | 0.51 | 46 |
| BAA-21b | 588 | 608 | 20 | 0.54 | 50 |
| BAA-22a | 585 | 602 | 17 | 0.39 | 49 |
| BAA-22b | 582 | 601 | 19 | 0.27 | 46 |
| BAA-23a | 592 | 603 | 11 | 0.23 | 30 |
| BAA-23b | 580 | 588 | 8 | 0.19 | 32 |
| BAA-24b | 570 | 579 | 9 | 0.29 | 32 |
| BAA-25a | 571 | 580 | 9 | 0.19 | 32 |
| BAA-25b | 572 | 580 | 8 | 0.18 | 32 |
| BAA-26b | 582 | 604 | 22 | 0.30 | 51 |
| BAA-27b | 575 | 588 | 13 | 0.33 | 35 |
| BAA-28a | 480 | 592 | 112 | 0.04 | 52 |
| BAA-28b | 580 | 598 | 18 | 0.58 | 43 |
| BAA-29b | 569 | 580 | 11 | 0.13 | 37 |
| BAA-30a | 607 | 643 | 36 | 0.43 | 58 |
| BAA-31b | 576 | 588 | 12 | 0.28 | 34 |
| BAA-32a | 574 | 584 | 10 | 0.23 | 32 |
| BAA-33a | 575 | 587 | 12 | 0.15 | 35 |
| BAA-34b | 570 | 581 | 11 | 0.96 | 31 |
| BAA-35b | 571 | 580 | 9 | 0.25 | 32 |
| BAA-36b | 579 | 592 | 13 | 0.35 | 37 |
| BAA-37a | 568 | 578 | 10 | 0.54 | 55 |
| BAA-37b | 569 | 578 | 9 | 0.55 | 30 |
| BAA-38a | 579 | 581 | 2 | 0.07 | 33 |
| BAA-39a | 606 | 657 | 51 | 0.19 | 79 |
| BAA-40b | 583 | 601 | 18 | 0.26 | 45 |
| BAA-41b | 582 | 602 | 20 | 0.36 | 47 |
| BAA-42a | 570 | 580 | 10 | 0.36 | 30 |
| BAA-43a | 569 | 579 | 10 | 0.45 | 31 |
| BAA-44b | 582 | 600 | 18 | 0.28 | 43 |
| BAA-45b | 570 | 579 | 9 | 0.50 | 30 |
| BAA-45a | 571 | 580 | 9 | 0.22 | 31 |
| BAA-46b | 572 | 585 | 13 | 0.61 | 33 |
| BAA-47a | 589 | 611 | 22 | 0.33 | 47 |
| BAA-48a | 603 | 641 | 38 | 0.45 | 60 |
| BAA-49b | 571 | 580 | 9 | 0.14 | 33 |
| BAA-50a | 571 | 581 | 10 | 0.28 | 33 |
| BAA-50b | 572 | 581 | 9 | 0.12 | 34 |
| BAA-51a | 594 | 607 | 13 | 0.06 | 42 |
| BAA-52a | 577 | 585 | 8 | 0.04 | 51 |
| BAA-53a | 570 | 581 | 11 | 0.44 | 30 |
| BAA-54a | 573 | 581 | 8 | 0.04 | 46 |
| BAA-55a | 576 | 592 | 16 | 0.75 | 35 |
| BAA-55b | 575 | 591 | 16 | 0.75 | 38 |
| BAA-56a | 585 | 595 | 10 | 0.91 | 32 |
| BAA-56b | 586 | 597 | 11 | 0.15 | 35 |
| BAA-57a | 574 | 590 | 16 | 0.75 | 45 |
| BAA-57b | 575 | 591 | 16 | 0.75 | 38 |
| BAA-58a | 572 | 582 | 10 | 0.70 | 30 |
| BAA-59a | 571 | 581 | 10 | 0.53 | 30 |
| BAA-60b | 588 | 604 | 16 | 0.47 | 37 |
| BAA-61a | 573 | 587 | 14 | 1.00 | 35 |
| BAA-62a | 579 | 594 | 15 | 0.68 | 33 |
| BAA-63a | 592 | 607 | 15 | 0.43 | 39 |
| BAA-64a | 576 | 593 | 17 | 0.80 | 37 |
| BAA-65a | 606 | 622 | 16 | 0.21 | 54 |
| BAA-66a | 587 | 598 | 11 | 0.28 | 34 |
| BAA-67a | 587 | 598 | 11 | 0.15 | 61 |
| BAA-68a | 585 | 595 | 10 | 0.17 | 30 |
| BAA-69a | 577 | 589 | 12 | 0.85 | 30 |
| BAA-70a | 580 | 588 | 8 | 0.17 | 33 |
| BAA-71a | 580 | 589 | 9 | 0.19 | 32 |
| BAA-72a | 580 | 590 | 10 | 0.40 | 31 |
| BAA-73a | 579 | 593 | 14 | 0.55 | 46 |
| BAA-74a | 584 | 602 | 18 | 0.15 | 59 |
| BAA-74b | 583 | 600 | 17 | 0.22 | 51 |
| BAA-75a | 614 | 663 | 49 | 0.08 | 91 |
| BAA-75b | 605 | 660 | 55 | 0.18 | 91 |
| BAA-76a | 613 | 634 | 21 | 0.21 | 55 |
| BAA-77a | 603 | 634 | 31 | 0.50 | 61 |
| BAA-78a | 581 | 592 | 11 | 0.19 | 46 |
| BAA-78b | 579 | 593 | 14 | 0.37 | 39 |
| BAA-79a | 606 | 630 | 24 | 0.63 | 49 |

Terms

Alkyl: a branched or unbranched saturated or unsaturated hydrocarbon group, such as, methyl, ethyl, n-propyl, isopropyl, n-butyl, isobutyl, t-butyl, pentyl, hexyl, heptyl, octyl, nonyl, decyl, tetradecyl, hexadecyl, eicosyl, tetracosyl and the like. A lower alkyl group is a saturated branched or unbranched hydrocarbon having from 1 to 6 carbon atoms ($C_{1-6}$ alkyl). Similarly, a $C_2$ or greater alkyl, a $C_3$ or greater alkyl, a $C_4$ or greater alkyl, etc. refers to a branched or unbranched saturated or unsaturated hydrocarbon group of two or more, three or more, four or more, etc. carbons. The term alkyl also encompasses cycloalkyls. Alkyl also encompasses substituted alkyls which are alkyl groups wherein one or more hydrogen atoms are replaced with a substituent such as, alkyl, alkynyl, alkenyl, aryl, halide, nitro, amino, ester, ether, ketone, aldehyde, hydroxyl, carboxyl, cyano, amido, haloalkyl, haloalkoxy, or alkoxy. The term alkyl also encompasses heteroalkyls. A heteroalkyl contains at least one heteroatom such as nitrogen, oxygen, sulfur, or phosphorus replacing one or more of the carbons. Substituted heteroalkyls are also encompassed by the term alkyl.

Amino: a saturated or unsaturated nitrogen group. An amino group includes an unsubstituted amino (—$NH_2$ or —$NH_3^+$) or substituted amino. A substituted amino generally has the structure —$NQ_1Q_2$ or —$NQ_1Q_2Q_3^+$ where at least one of $Q_1$, $Q_2$ and $Q_3$ are selected from an alkyl (including a substituted alkyl) as described above or any other substituent including, for example, alkynyl, alkenyl, aryl, halide, nitro, amino, ester, ether, ketone, aldehyde, hydroxyl, carboxyl, cyano, amido, haloalkyl, haloalkoxy, or alkoxy. Examples of substituted amino groups include the following structures: —$NHCH_3$, —$N(CH_3)_2$—$NH(CH_3)_2^+$—$N(CH3)_3^+$, $NHCH_2CH_3$, $NH_2CH_2CH_3+$, $NCH_3CH_2CH_3$, $N(CH_2CH_3)_2$, $NHCH_3CH_2CH_3^+$. Amino groups also include cyclic structures and structures including other heteroatoms such as oxygen, sulfur or phosphorus. Cyclic amino structures include 4-member single nitrogen (azetidinyl), 5-member single nitrogen (pyrrolidinyl), or 6-member single nitrogen (piperidinyl) structures as well as double nitrogen structures, as well as substituted cyclic amino structures.

Aryl: any carbon-based aromatic group including, benzyl, naphthyl, and phenyl. The term aryl also contemplates substituted aryls in which one or more of the hydrogens is substituted with one or more groups including alkyl, alkynyl, alkenyl, aryl, halide, nitro, amino, ester, ether, ketone, aldehyde, hydroxy, carboxylic acid, cyano, amido, haloalkyl, haloalkoxy, or alkoxy. The term aryl also contemplates heteroaryls in which one or more of the carbons is replaced by a heteroatom. Examples of heteroatoms include, nitrogen, oxygen, sulfur, and phosphorous. Substituted heteroaryls are also encompassed by the term aryl.

Cycloalkyl: a non-aromatic carbon-based ring composed of at least three carbon atoms. Examples of cycloalkyl groups include cyclopropyl, cyclobutyl, cyclopentyl, and cyclohexyl. Cycloalkyls also encompass substituted cycloalkyls and heterocycloalkyls where at least one of the carbon atoms is replaced with a heteroatom such as nitrogen, sulfur or phosphorus. A heterocycloalkyl wherein one or more of the carbons is replaced with nitrogen is also termed a cycloalkylamino herein. The term also encompasses substituted heterocycloalkyls.

Heterocycle: A group that encompasses both heteroaryls and heterocycloalkyls. Heteroaryls can also be termed aromatic heterocycles. Heterocycles may be monocyclic or polycyclic rings. Exemplary heterocycles include azepinyl, aziridinyl, azetyl, azetidinyl, diazepinyl, dithiadiazinyl, dioxazepinyl, dioxolanyl, dithiazolyl, furanyl, isooxazolyl, isothiazolyl, imidazolyl, morpholinyl, oxetanyl, oxadiazolyl, oxiranyl, oxazinyl, oxazolyl, piperazinyl, pyrazinyl, pyridazinyl, pyrimidinyl, piperidyl, piperidino, pyridyl, pyranyl, pyrazolyl, pyrrolyl, pyrrolidinyl, thiatriazolyl, tetrazolyl, thiadiazolyl, triazolyl, thiazolyl, thienyl, tetrazinyl, thiadiazinyl, triazinyl, thiazinyl, thiopyranyl, furoisoxazolyl, imidazothiazolyl, thienoisothiazolyl, thienothiazolyl, imidazopyrazolyl, cyclopentapyrazolyl, pyrrolopyrrolyl, thienothienyl, thiadiazolopyrimidinyl, thiazolothiazinyl, thiazolopyrimidinyl, thiazolopyridinyl, oxazolopyrimidinyl, oxazolopyridyl, benzoxazolyl, benzisothiazolyl, benzothiazolyl, imidazopyrazinyl, purinyl, pyrazolopyrimidinyl, imidazopyridinyl, benzimidazolyl, indazolyl, benzoxathiolyl, benzodioxolyl, benzodithiolyl, indolizinyl, indolinyl, isoindolinyl, furopyrimidinyl, furopyridyl, benzofuranyl, isobenzofuranyl, thienopyrimidinyl, thienopyridyl, benzothienyl, cyclopentaoxazinyl, cyclopentafuranyl, benzoxazinyl, benzothiazinyl, quinazolinyl, naphthyridinyl, quinolinyl, isoquinolinyl, benzopyranyl, pyridopyridazinyl and pyridopyrimidinyl groups. The term also contemplates substituted heterocycles, including substituted forms of all the species listed above.

Fluorescent Dye: a small molecule that absorbs light at one wavelength and then emits light at a second wavelength. Dyes of different structure emit at different wavelengths and, as a result, multiple fluorescent dyes can be distinguishable from one another and can label multiple targets simultaneously. The compositions disclosed herein can be used as fluorescent dyes.

Scheme 1
Synthesis of BAA Library

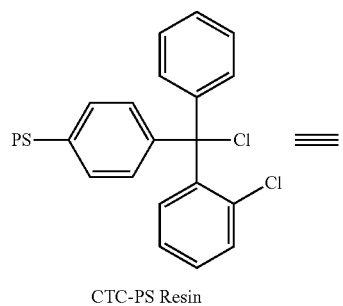

CTC-PS Resin

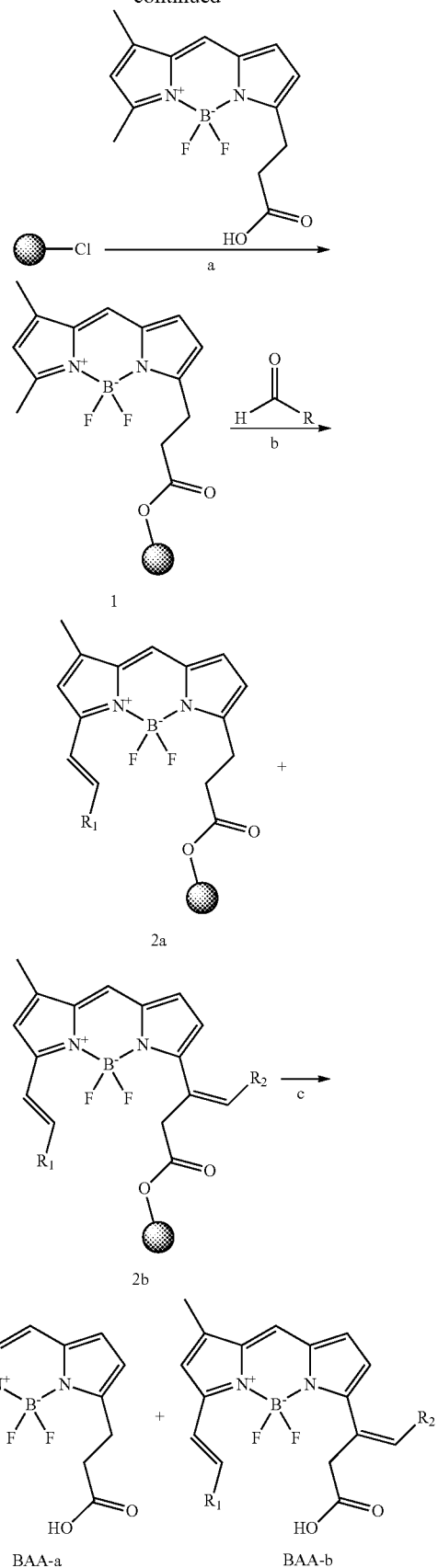

Reagents and Conditions: (a) DCM, DIEA, rt, 20 h; (b) R-CHO (79 aromatic aldehydes shown in the tables herein), DMSO-ACN (1:1), pyrrolidine, acetic acid, 85° C., 15 min; (c) TFA-DCM (0.5:99.5), rt, 2×10 min.

Experimentals

Materials. All commercially available starting materials were used without further purification unless otherwise stated. 4,4-Difluoro-5,7-Dimethyl-4-Bora-3a,4a-Diaza-s-Indacene-3-Propionic Acid (BODIPY FL) was obtained from Thermo Fisher Scientific. Aromatic aldehydes were purchased from Thermo Fisher Scientific and Sigma-Aldrich. 2-Chlorotrityl chloride polystyrene (CTC-PS) 100-200 mesh resin was purchased from EMD-Millipore. ACN and water for HPLC and LC/MS were purchased from Thermo Fisher Scientific at LC/MS purity grade.

General Instruments. Synthesized sample purification was performed with an Agilent 1260 Infinity HPLC utilizing a C18 column (150 mm×21.2 mm). MS (HRMS, ESI) spectra data was collected with an Agilent 6244 TOF LC/MS with diode array detector VL+ and C18 column (4.6 mm×50 mm). Absorbance and fluorescence data were measured on a SpectraMax M5 Microplate reader. NMR spectra, $^1$H and $^{13}$C, were recorded on a Bruker ARK400 spectrometer. BAA microscopy screening in cells for organelle specificity and signal-to-background ratio was completed with an Axio Zeiss Light Microscope and 63× oil immersion objective.

General Procedure for the Synthesis of BAA Fluorophore Library BODIPY FL was loaded onto CTC-PS resin in the following increments: 500 mg of BODIPY FL in 17.2 ml of DCM added to 5 g of CTC-PS resin in 14.9 ml of DIEA, protected from light on shaker overnight, washed 3×DCM, 3×DMF, 3×MeOH, 3×DMF, 3×DMC and dried with ethyl ether, resulting in 90% BODIPY FL retained on resin. BODIPY FL loaded CTC-PS resin (100 mg in 3 ml of 1:1 DMOS:ACN) and 15 equiv aldehyde (0.45 mmol in 1 ml 1:1 DMSO:ACN) were mixed with 65 equivalent acetic acid (105 µl, 2 mmol) and 65 equivalent pyrrolidine (150 µl, 2 mmol) at 85° C. for 15 min. The resin was washed 3×(3× DMC, 3×DMF), 3×ethyl ether before cleaving the formed BAA compound with 0.5% TFA in DCM. The BAA compounds were purified via HPLC and dried with Labconco freeze dryer.

Characterization of BAA Library. All BAA compounds were characterized by LC/MS for m/z ratio and purity. Marvin Sketch was used for chemical characterization of structures. Molecular orbital calculations were performed using the density functional theory (DFT) at B3LYP/6-31G level. The six BAA compounds selected for CLSM imaging were characterized further by $^1$H and $^{13}$C NMR (See Supporting Information).

Fluorescence Properties and Quantum Yield Measurements. Spectroscopic characterizations were performed in anhydrous DMSO in polystyrene 96 well plate. Analysis included the maximum absorbance wavelength, maximum fluorescence emission wavelength, full-width-at half max, and quantum yield. Quantum yields ($\phi_{fl}$) were determined by comparing the area under the emission spectrum of the BAA compound to a reference fluorophore solution at three concentrations using equation 1, where Grad represents the gradient from the plots of integrated fluorescence intensity vs absorbance at three concentrations and η is the refractive index of the solvent. Fluorescein in 0.1 M NaOH ($\phi_{fl}$=0.91)$^3$ was the reference for samples with a max absorbance up to 510 nm, where an excitation of 470 nm was used with the emission integrated between 490 to 800 nm. Rhodamine B in ethanol ($\phi_{fl}$=0.70) was the reference for samples with a max absorbance between 511-595 nm, where an excitation of 525 nm was used with the emission integrated between 545 to 800 nm. Cresyl violet in methanol ($\phi_{fl}$=0.54)$^4$ was the reference for samples with a max absorbance above 595 nm, where an excitation of 570 nm was used with the emission integrated between 590 to 800 nm.

$$\Phi_{fl}^{sample} = \Phi_{fl}^{reference} \left( \frac{\text{Grad}^{sample}}{\text{Grad}^{reference}} \right) \left( \frac{\eta^{sample}}{\eta^{reference}} \right)^2 \tag{1}$$

Cell Culture. U2OS cells were cultured in Dulbecco's Modified Eagle Medium without phenol red (Invitrogen) supplemented with 10% fetal bovine serum and 1% Penicillin-Streptomycin-Glutamine at 37° C. and 5% $CO_2$. Cells were plated in a 96-well glass bottom plate and incubated for 3 days to reach 50% confluency.

Microscopy Screening for Organelle Specificity in Cells. Cells were preextracted with 0.5% Triton X-100 in PBS for 20 s, fixed with 0.4% glutaldehyde (GA, Electron Microscopy Science) and 0.25% Triton X-100 in PBS for 90 s, and washed with PBS before fixing with 3% GA in PBS for 15 min. Cells were washed with PBS (3×5 min), reduced with 10 mM sodium borohydride for 10 min, washed again with PBS (3×5 min), and blocked with 5% bovine serum albumin (BSA) in PBS for 10 min. BAA compounds were diluted to 10 µM in PBS for organelle screening and incubated with permeabilized fixed cells for 5 min, washed with PBS and imaged at 60× magnification.

The following are incorporated by reference herein:
a. Demas J N and Crosby G A, *J Phys Chem* 75, 991 (1971);
b. Douglas M and Brannon J H, *J Phys Chem* 83, 696 (1979);
c. Karstens T and Kobs K J, *J Phys Chem* 84, 1871 (1980).

As will be understood by one of ordinary skill in the art, each embodiment disclosed herein can comprise, consist essentially of or consist of its particular stated element, step, ingredient or component. Thus, the terms "include" or "including" should be interpreted to recite: "comprise, consist of, or consist essentially of." The transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Definitions and explanations used in the present disclosure are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Ed. Anthony Smith, Oxford University Press, Oxford, 2004).

The invention claimed is:

1. A compound with the structure:

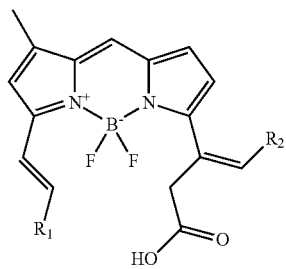

where $R_1$ is aryl, substituted aryl, aromatic heterocycle, or substituted aromatic heterocycle and where $R_2$ is H, aryl, substituted aryl, aromatic heterocycle, or substituted aromatic heterocycle.

2. The compound of claim 1 with the structure:

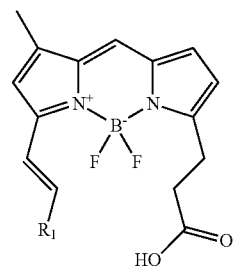

where $R_1$ is substituted or unsubstituted quinolinyl, substituted or unsubstituted isoquinolinyl, substituted or unsubstituted indolyl, substituted or unsubstituted benzyl, substituted or unsubstituted naphthyl, substituted or unsubstituted pyrimidinyl, substituted or unsubstituted thiophenyl, substituted or unsubstituted pyrazolyl, substituted or unsubstituted thiazolyl, substituted or unsubstituted pyridinyl, or substituted or unsubstituted furanyl.
3. The compound of claim 2 where $R_1$ is selected from:
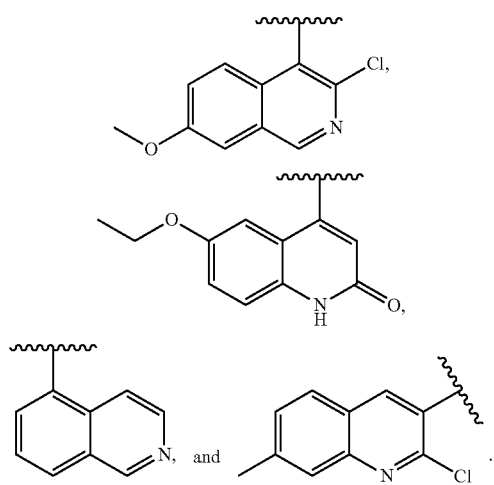
4. The compound of claim 2 where $R_1$ is selected from:
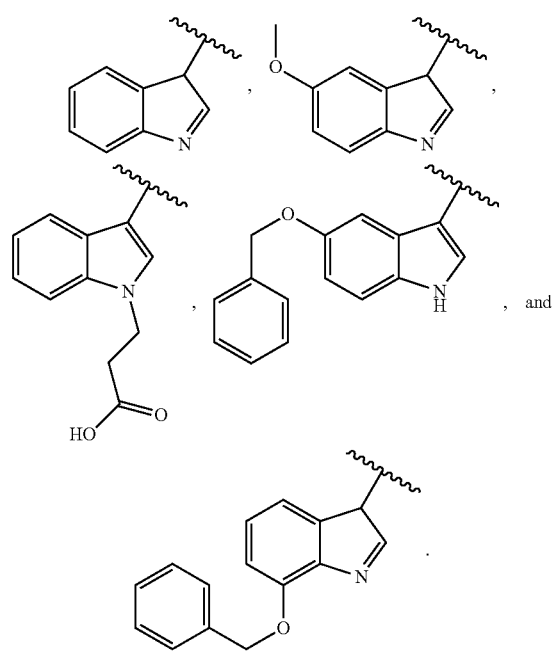
5. The compound of claim 2 where $R_1$ is selected from:
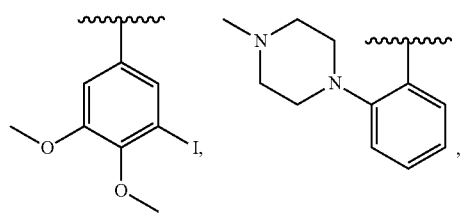
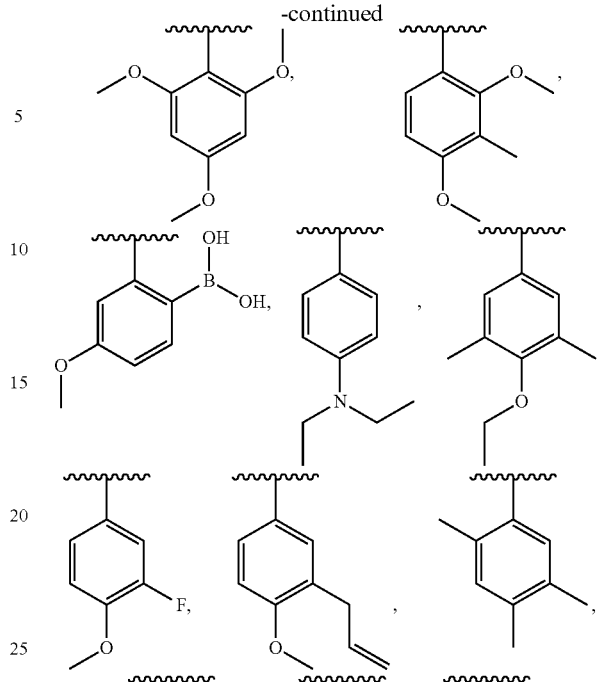
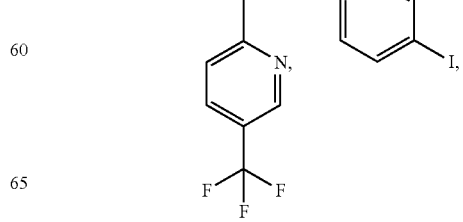

-continued
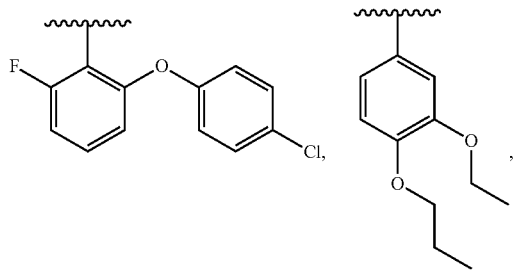
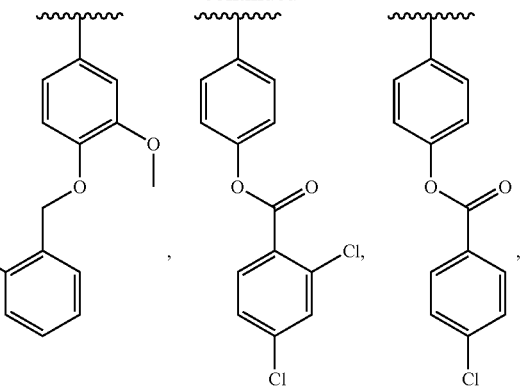
-continued
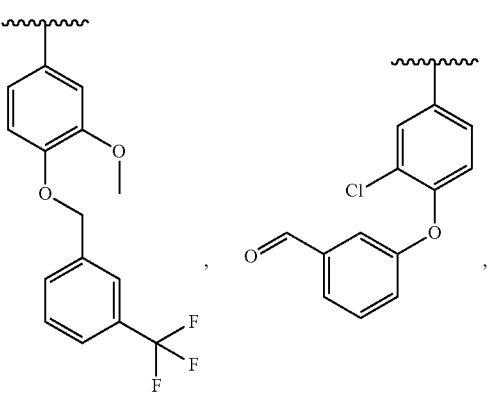
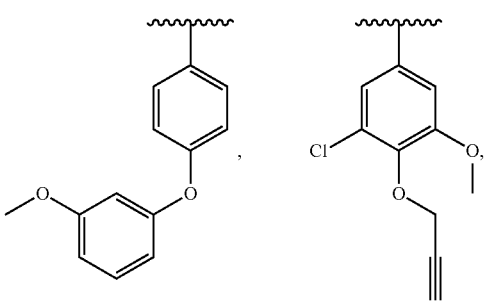
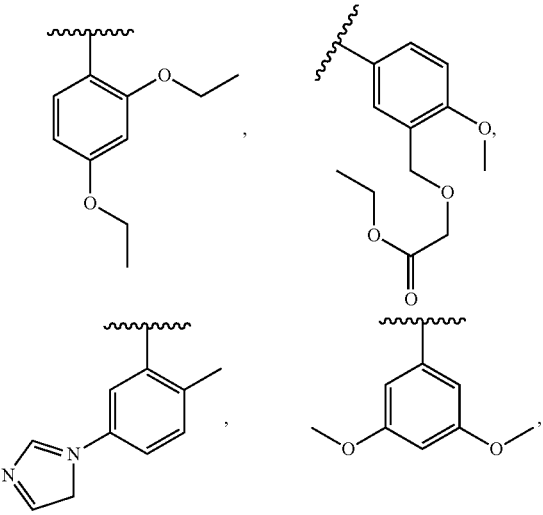

-continued
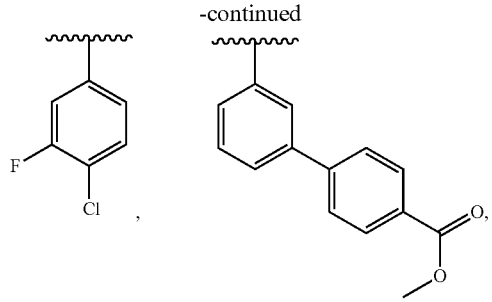
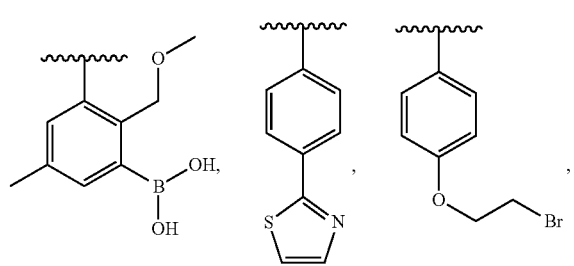
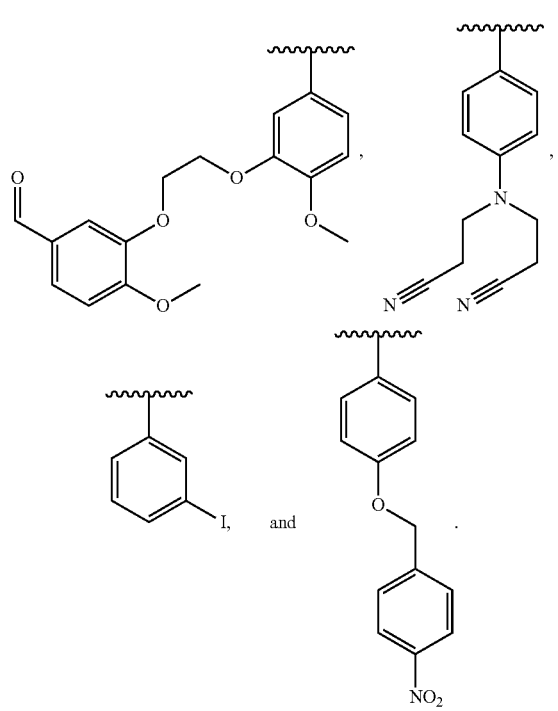
6. The compound of claim 2 where $R_1$ is
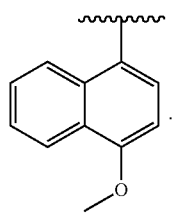
7. The compound of claim 2 where $R_1$ is selected from
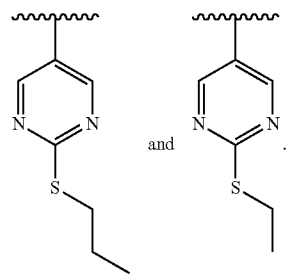
and
8. The compound of claim 2 where $R_1$ is selected from
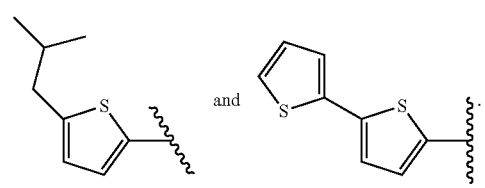
and
9. The compound of claim 2 where $R_1$ is selected from
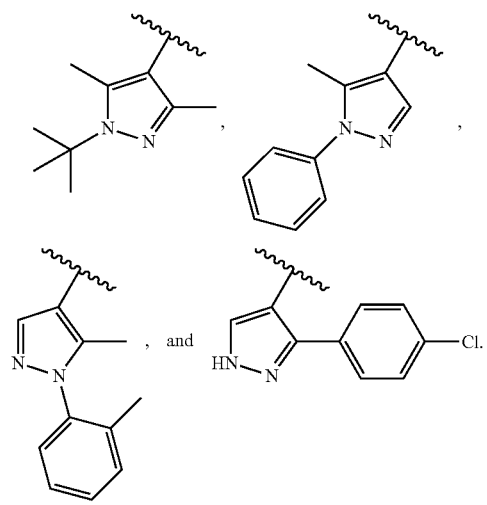
, and
10. The compound of claim 2 where $R_1$ is:
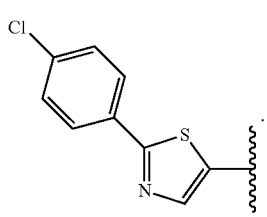 [SMILES: *c1cnc(-c2ccc(Cl)cc2)s1]

11. The compound of claim 2 where $R_1$ is selected from:

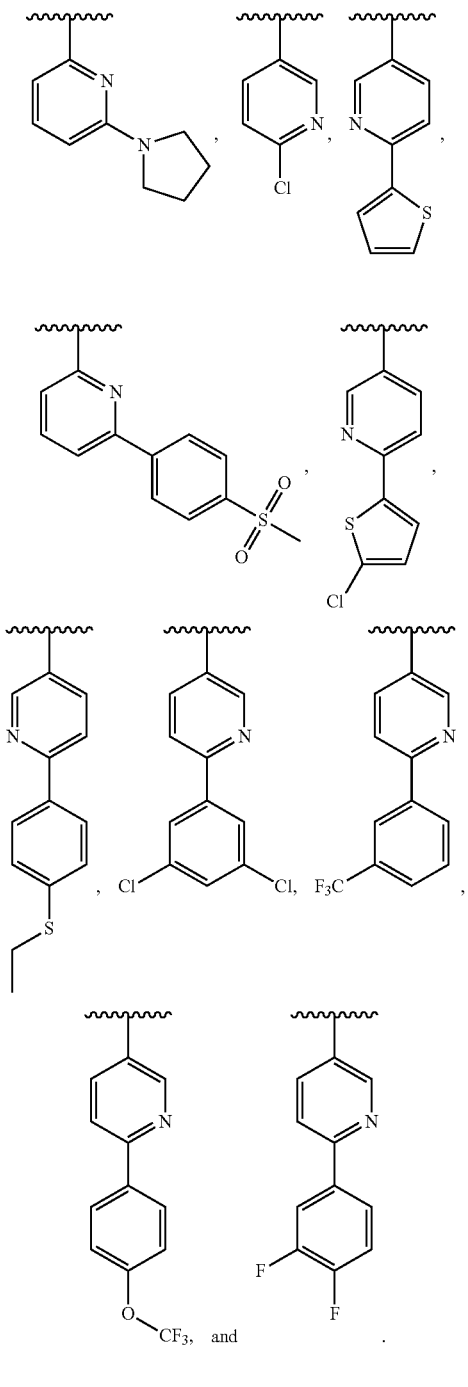

12. The compound of claim 2 where $R_1$ is selected from:

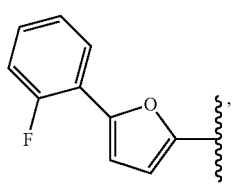

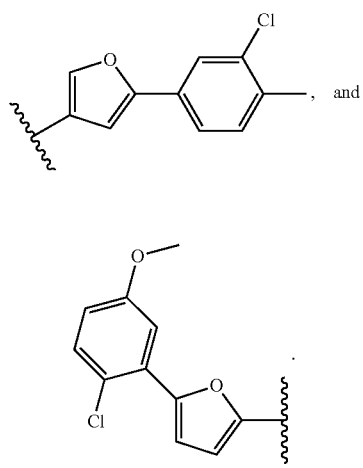

13. The compound of claim 1 where $R_1$ and $R_2$ are independently substituted or unsubstituted quinolinyl, substituted or unsubstituted isoquinolinyl, substituted or unsubstituted indolyl, substituted or unsubstituted benzyl, substituted or unsubstituted naphthyl, substituted or unsubstituted pyrimidinyl, substituted or unsubstituted thiophenyl, substituted or unsubstituted pyrazolyl, substituted or unsubstituted thiazolyl, substituted or unsubstituted pyridinyl, or substituted or unsubstituted furanyl.

14. The compound of claim 13 where $R_1$ and $R_2$ are both substituted or unsubstituted quinolinyl, substituted or unsubstituted isoquinolinyl, substituted or unsubstituted indolyl, substituted or unsubstituted benzyl, substituted or unsubstituted naphthyl, substituted or unsubstituted pyrimidinyl, substituted or unsubstituted thiophenyl, substituted or unsubstituted pyrazolyl, substituted or unsubstituted thiazolyl, substituted or unsubstituted pyridinyl, or substituted or unsubstituted furanyl.

15. The compound of claim 14 where $R_1$ and $R_2$ are both substituted or unsubstituted quinolinyl or isoquinolinyl and selected from:

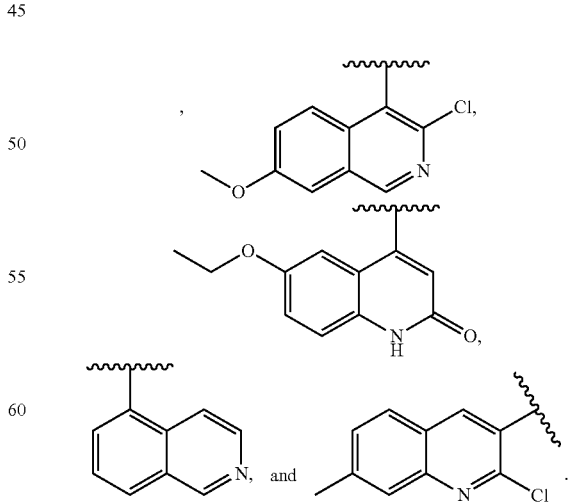

16. The compound of claim 14 where $R_1$ and $R_2$ are both substituted or unsubstituted indolyl and are selected from:

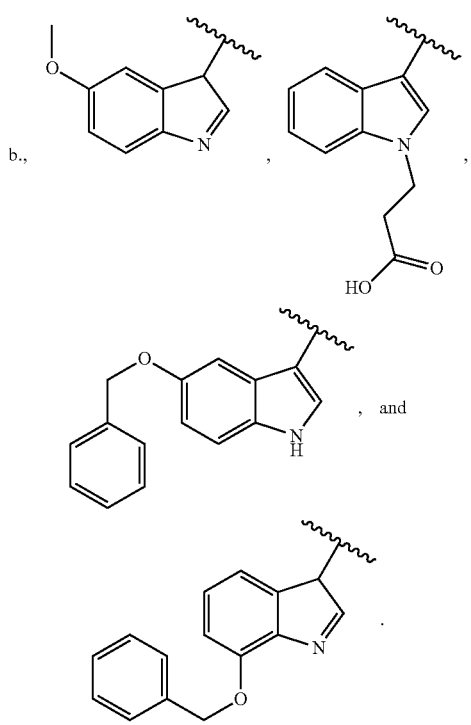
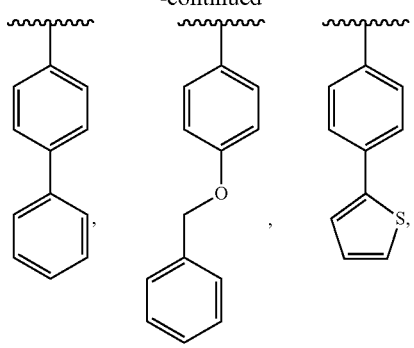
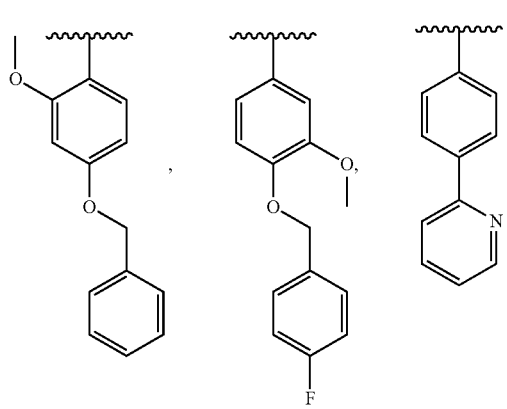
17. The compound of claim 14 where $R_1$ and $R_2$ are both substituted or unsubstituted benzyl and are selected from:
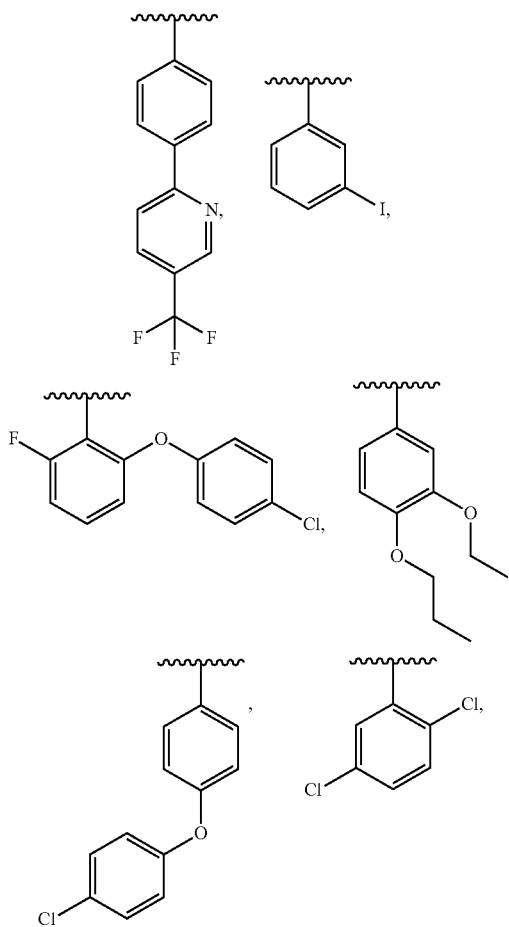

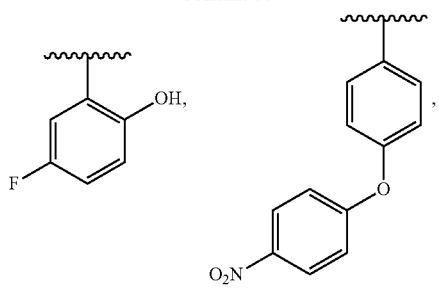
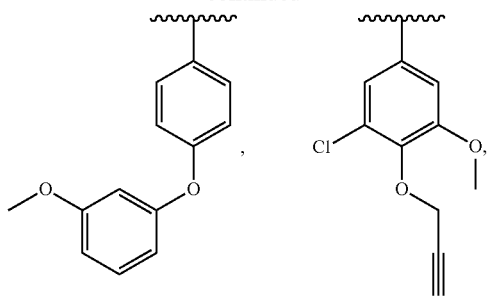

-continued

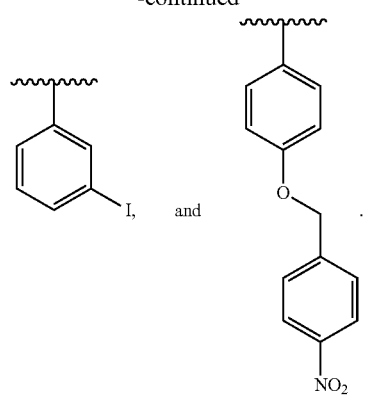

18. The compound of claim 14 where $R_1$ and $R_2$ are both

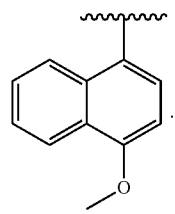 [SMILES: *c1ccc(OC)c2ccccc12]

19. The compound of claim 14 where $R_1$ and $R_2$ are both substituted or unsubstituted pyrimidinyl and are selected from:

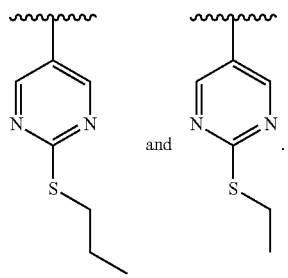

20. The compound of claim 14 where $R_1$ and $R_2$ are both substituted or unsubstituted thiophenyl and are selected from

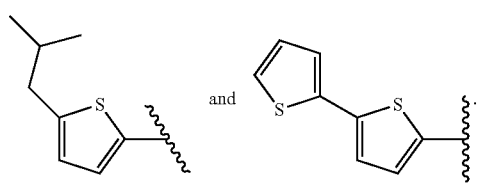

21. The compound of claim 14 where $R_1$ and $R_2$ are both substituted or unsubstituted pyrazolyl and are selected from

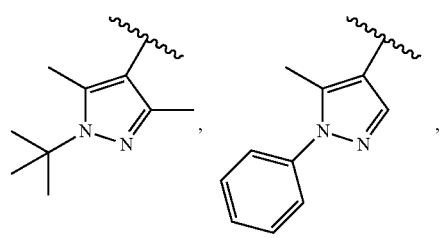

-continued

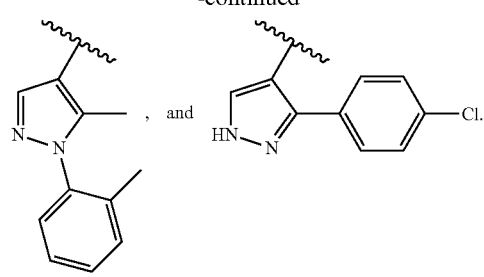

22. The compound of claim 14 where $R_1$ and $R_2$ are both:

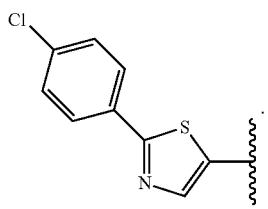 [SMILES: *c1cnc(-c2ccc(Cl)cc2)s1]

23. The compound of claim 14 where $R_1$ and $R_2$ are both substituted or unsubstituted pyridinyl and are selected from:

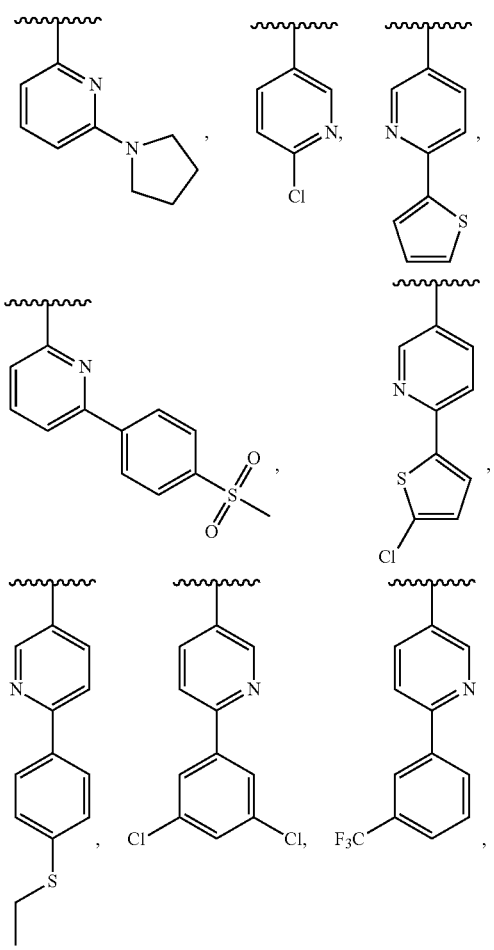

US 9,751,897 B1
61
-continued
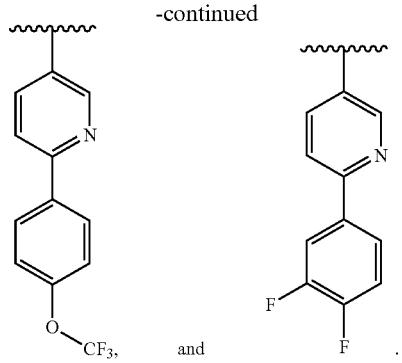
24. The compound of claim 14 where $R_1$ and $R_2$ are both substituted or unsubstituted furanyl and are selected from:
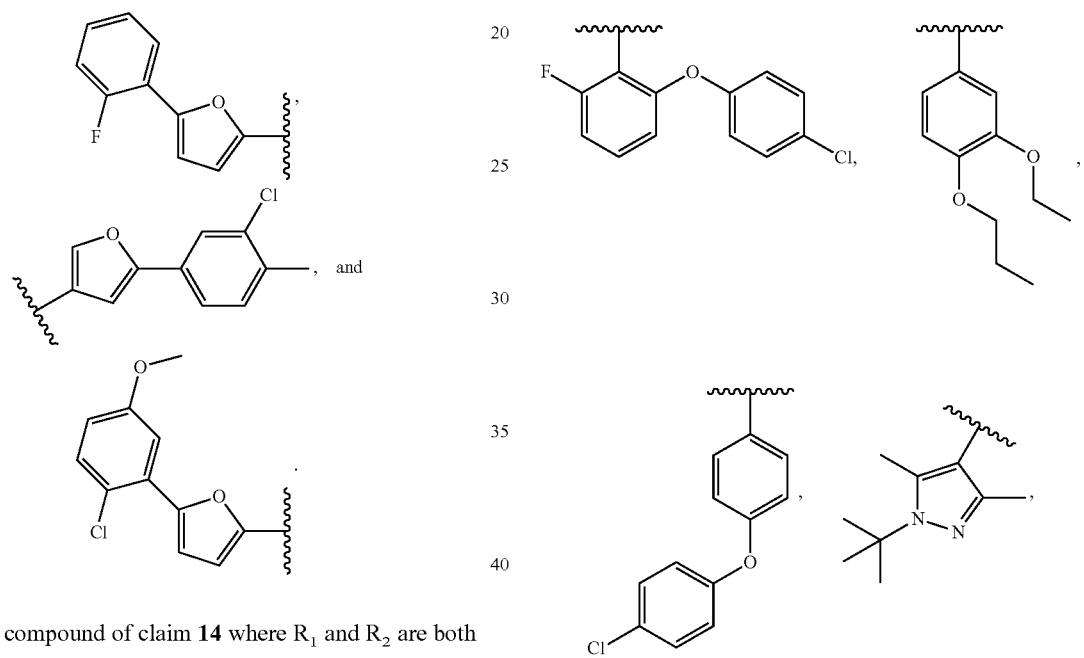
25. The compound of claim 14 where $R_1$ and $R_2$ are both selected from:
62
-continued
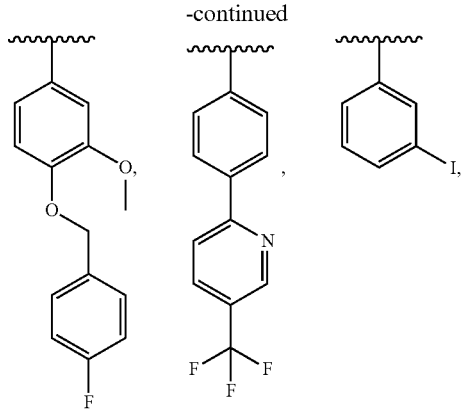
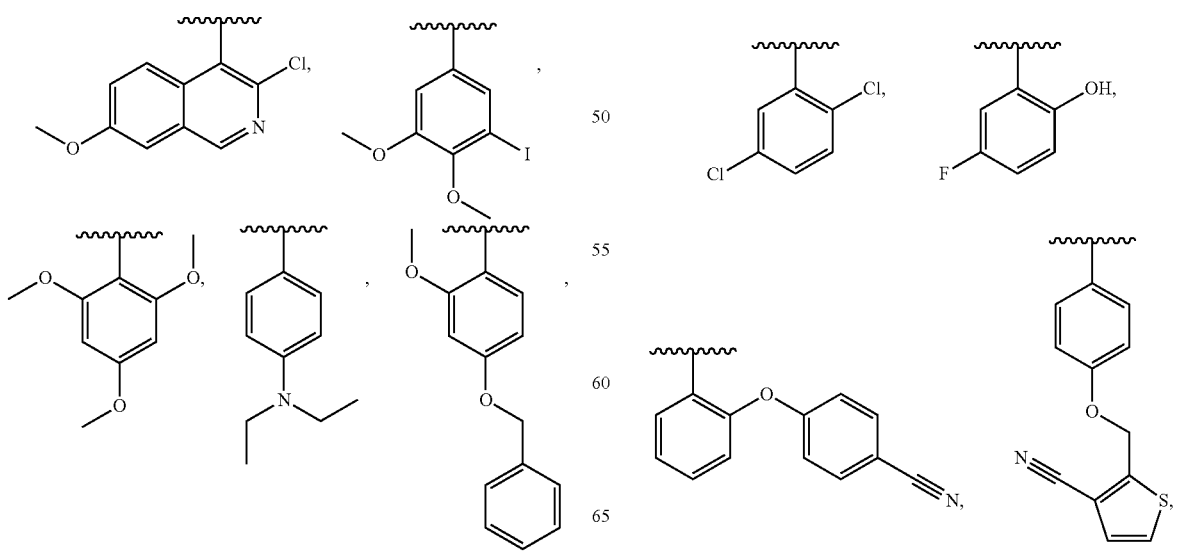

-continued
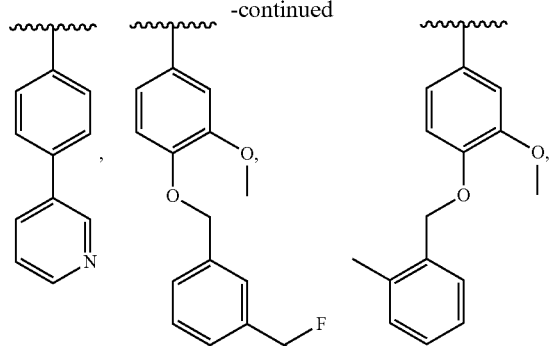
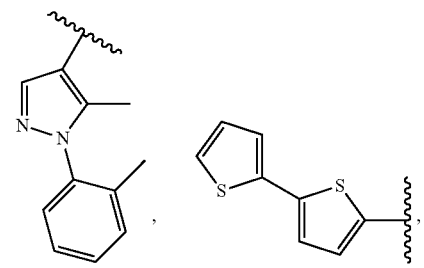
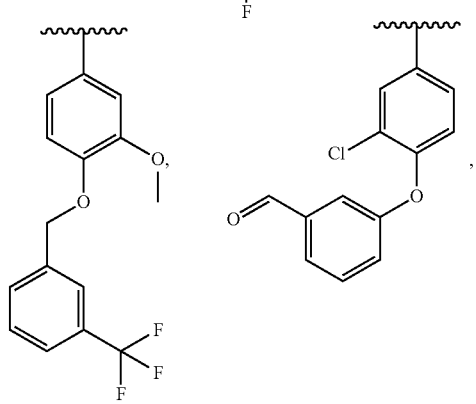
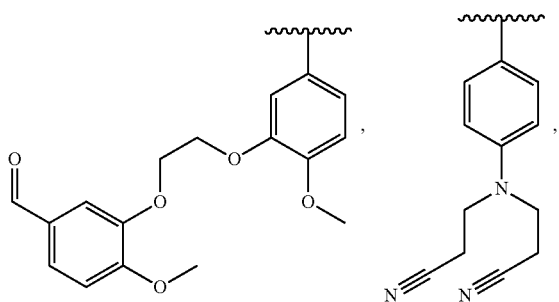
and
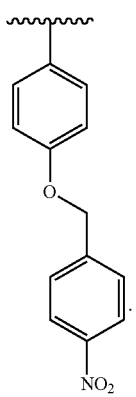
* * * * *